US012758678B2

(12) United States Patent
Potreck

(10) Patent No.: US 12,758,678 B2
(45) Date of Patent: Oct. 13, 2026

(54) MULTI-COMPONENT SYSTEM

(71) Applicant: COSA Group GmbH, Munich (DE)

(72) Inventor: Janine-Melanie Potreck, Munich (DE)

(73) Assignee: COSA Group GmbH, Munich (DE)

( * ) Notice: Subject to any disclaimer, the term of this patent is extended or adjusted under 35 U.S.C. 154(b) by 538 days.

(21) Appl. No.: 18/246,315

(22) PCT Filed: Sep. 24, 2021

(86) PCT No.: PCT/EP2021/076416

§ 371 (c)(1),
(2) Date: Mar. 22, 2023

(87) PCT Pub. No.: WO2022/064014

PCT Pub. Date: Mar. 31, 2022

(65) Prior Publication Data

US 2023/0390450 A1 Dec. 7, 2023

(30) Foreign Application Priority Data

Sep. 24, 2020 (DE) ..................... 10 2020 124 995.0

(51) Int. Cl.
*A61L 24/00* (2006.01)

(52) U.S. Cl.
CPC ....... *A61L 24/0073* (2013.01); *A61L 24/0015* (2013.01)

(58) Field of Classification Search
CPC ......................... A61L 24/0073; A61L 24/0015
See application file for complete search history.

(56) References Cited

U.S. PATENT DOCUMENTS

| | | | | |
|---|---|---|---|---|
| 8,117,795 | B2 | 2/2012 | Knauseder | |
| 2004/0109894 | A1 | 6/2004 | Shefer et al. | |
| 2007/0021533 | A1 | 1/2007 | Yan et al. | |
| 2007/0087049 | A1 * | 4/2007 | Clarke ...................... | A61J 3/07 424/451 |
| 2018/0037749 | A1 | 2/2018 | Wilson et al. | |
| 2018/0280913 | A1 * | 10/2018 | Kobilka .................. | B01J 13/20 |

FOREIGN PATENT DOCUMENTS

| | | |
|---|---|---|
| DE | 10 2006 013 678 | 9/2007 |
| WO | 01/94721 | 12/2001 |
| WO | 02/060573 | 8/2002 |
| WO | 2014/135689 | 9/2014 |

OTHER PUBLICATIONS

International Search Report dated Jun. 22, 2022, in PCT/EP2021/076416, with English translation, 16 pages.
Written Opinion dated Jun. 22, 2022, in PCT/EP2021/076416, with English translation, 18 pages.

* cited by examiner

*Primary Examiner* — Shirley V Gembeh
(74) *Attorney, Agent, or Firm* — Grüneberg Global IP, PLLC

(57) ABSTRACT

A multi-component system contains at least one first substance and at least one second substance, where the first substance and the second substance are present in one or more substance portions.

13 Claims, 21 Drawing Sheets

MULTI-COMPONENT SYSTEM

CROSS-REFERENCE TO RELATED APPLICATIONS

This application is the National Stage entry under § 371 of International Application No. PCT/EP2021/076416, filed on Sep. 24, 2021, and which claims the benefit of priority to German Application No. 10 2020 124 995.0, filed on Sep. 24, 2020. The content of each of these applications is hereby incorporated by reference in its entirety.

BACKGROUND OF THE INVENTION

Field of the Invention

The present invention relates to a multi-component system. In particular, the present invention relates to a multi-component system in which the various components can be activated at different time points. In addition, the present invention relates to the use as a multi-component adhesive system, and to the use of the system according to the invention for medical and other purposes.

Description of Related Art

From the prior art, multi-component systems are already known.

For example, multi-component systems are used in adhesive technology, such as two-component systems.

An adhesive structure is known from U.S. Pat. No. 9,333,725B2, the adhesive structure includes a first layer, a second layer, and a hybrid adhesive layer for bonding the first layer to the second layer. The hybrid adhesive layer contains two or more adhesive units made of different adhesive materials; the two or more adhesive units are arranged in a pattern.

It is desirable, by combining at least two different adhesive compositions having the same and/or different properties, to combine these properties in such a way that the different adhesive properties combine and preferably also reinforce each other.

SUMMARY OF THE INVENTION

It is the task of the present invention to further develop a multi-component system in an advantageous manner, in particular in that an improved effect is achieved through the combination of several components, in particular compared to the use of the individual components. In particular, a multi-component adhesive system is to be used to achieve an improved adhesive effect, in particular compared with the use of the individual components. It is also a task of the present invention to provide a multi-component system in which the individual components of the system can be activated at defined time points in order to improve or utilize the advantageous properties of the system or systems.

This task is solved according to the invention by a multi-component system having the features as described below, according to which it is provided that a multi-component system is provided with at least one first substance N1 and with at least one second substance N2, wherein the first substance and the second substance can be present in one or more substance portions.

DETAILED DESCRIPTION OF THE INVENTION

Figure 1:
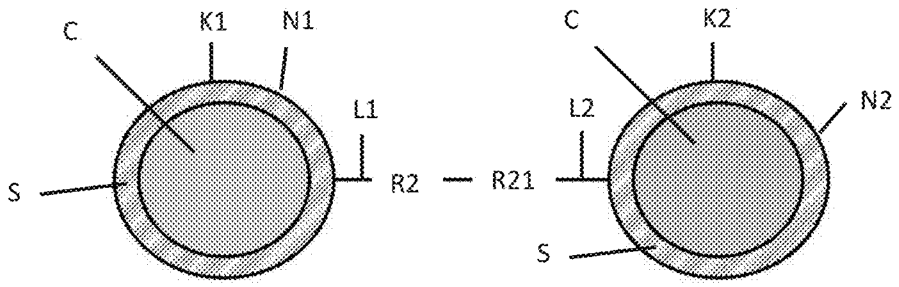
FIG. 1 shows an embodiment of a multi-component system according to the invention with a first substance and a second substance.

The invention is based on the basic idea that at least one property of the at least one first substance can be combined with at least one property of the at least one second substance, and thus an advantage is achieved compared to the use of the individual substances. Thereby, for example, in one embodiment, at least one first adhesive can be combined with at least one second adhesive, and thus improved properties, such as improved adhesive strength or also improved sealing with, for example, the same adhesive strength, can be achieved than when the individual adhesives are used separately. The multi-component system can thus comprise a hybrid adhesive.

In general, the multi-component system can comprise two or more than two substances.

In one embodiment, a multi-component adhesive system can thus achieve improved adhesion compared to a one-component adhesive system, particularly when bonding different surfaces or materials. For example, an improved bonding of a metal surface (for example a surface of a heavy metal, light metal, noble metal, semi-noble metal, alloy or base metal) with a plastic surface and/or a wood surface and/or paper surface and/or textile surface, fabric, yarn, suture material, fiber composites can be achieved compared to the use of a single adhesive.

Improved bonding can comprise improved (increased and/or more durable and/or longer lasting and/or non-water soluble) adhesion.

The total effect of the sum of the properties of the two or more substances can thereby also be greater than the sum of the partial effects of the properties of the individual substances, if these are used individually.

In one embodiment, however, the first substance can be an adhesive and/or the second substance can be a substance other than an adhesive.

Adhesives used can comprise, but are not limited to, for example epoxy adhesives and/or silicone adhesives and/or polyurethane adhesives and/or acrylate adhesives and/or fibrin adhesives, phase change material.

However, substances can also be used which not only have adhesive properties but also, for example, substances such as sealants which also have a beneficial function for the materials or surfaces to be bonded. Sealants such as silicones, acrylic resin dispersions or the like can be used.

The properties of the substances may include, for example, insulating, thermally conductive, electrically conductive, antibiotic, antimicrobial, adhesive, tackifying, activating, inhibiting, blocking, sealing, water soluble and/or luminescent properties. For example, in a multi-component adhesive system, the combination of multiple adhesives can provide improved adhesive effect compared to using the individual adhesives. Alternatively and/or additionally, the adhesive effect of a first substance can be combined with, for example, a sealing effect of a second substance.

The substances or substance portions can generally comprise (nano- and/or micro)-capsules, (adhesive)-dots, as well as geometric or non-geometric shapes, stripes, spheres, ellipses, lines, tracks, etc. formed from dots. In this context, nanocapsules typically have a size in the nanometer range (i.e., size smaller than 1000 nm), while microcapsules can also have capsules in the size range of a few millimeters, such as up to 2 mm. The terms substance and substance portion are used synonymously in the present application.

In general, the substances are placed in the core (also referred to as nucleus) of the respective capsules and are surrounded by one or more shells. These substances can be in solid, liquid or gaseous form.

The capsules can be linked to one another via a bridge. Preferably, the capsules are covalently linked via a bridge.

In certain embodiments, the capsule shell is functionalized. Functionalization of the capsule is typically accomplished by attaching a linker (L) to the capsule shell and, optionally, a functional group attached to the linker. However, the functionalization can also be introduced directly during the preparation of the capsules, e.g. by means of UV radiation. Via reactions or interactions, different functional groups can link two capsules. This linkage can be formed, for example. In the form of a covalent bond when the two functional groups of the capsules react with each other. In these cases, the bridge that creates the linkage between both capsules is formed via the functional groups and the linkers that can optionally be attached to the capsules.

In particular, it is conceivable that the volume of the one or more substance portions of the first substance is in a defined ratio to the volume of the one or more substance portions of the second substance, such that when the one or more substance portions of the first substance are mixed with the one or more substance portions of the second substance, a defined mixing ratio of the substances is achieved. In particular, the volumes and the mixing ratio can be selected in such a way that the product of the mixing of the substances results in an effect that goes beyond the effect of the individual substances. In the case of an adhesive system, for example, an improved adhesion effect can result. Alternatively and/or additionally, the mixing ratio can be selected in such a way that the drying time of the hybrid adhesive is shortened.

In one embodiment, the first capsules are formed with at least one first functional group and optionally provided with a first linker, and the second capsules are formed with at least one second functional group and optionally provided with a second linker, wherein the first functional group reacts with the second functional group via a predefined interaction, via weak or strong interaction, but preferably via covalent bonding, and links them to each other, and wherein the distance of the functional groups to the respective capsules is determined by the respective linker (if present). It is clarified that the functional groups can also be linked directly to the shell of the capsule and no presence of a linker is required.

The advantage of this is that at least one first substance and at least one second substance can be arranged in a defined manner in relation to each other by means of the functional groups and, if present, the linkers and the linkage through the functional groups. In other words, the two substances in the capsules can be brought into a defined spatial arrangement so that, for example, a specific reaction of the first substance with the second substance is enabled. Thus, it is now possible to arrange the first substance and the second substance separately from each other in a defined ratio and correspondingly defined distance. Through appropriate activation, the substances are then mixed with each other and the reaction of the substances with each other is enabled.

In principle, it is also conceivable that the first and the second substance are identical, so that a one-component system exists. Such systems are also to be understood as multi-component systems in the above sense.

Furthermore, it can be provided that the first linker is longer than the second linker or vice versa. This has the advantage that, for example, the first substances are spaced further apart from each other than the first substance is spaced apart from the second substance. This results in the second substance always being spatially arranged between the first substances, which favors mixing. This also favors an adjustment of the concentration and/or volume ratios of the substances relative to each other.

A linker can be any form of linkage between a capsule and a functional group.

A linker can also be any type of direct linkage between a capsule and a functional group.

A bridge can be any type of direct linkage between two capsules. Thereby, the bridge can include the linkers and the functional groups.

In one embodiment, the first substance portions are formed with at least one first functional group and the second substance portions are formed with at least one second functional group, wherein the first functional group reacts with the second functional group via a predefined interaction, in particular via weak or strong interaction, but preferably via covalent bonding, and links them to each other, wherein the volume ratio of the first and second substance portions can be adjusted via the size/quantity of the two substance portions.

Substances or substances portions that may be contained in at least one of the capsules are preferably selected from the list of adhesives, pharmaceutically active ingredients, fragrances, dyes, fillers, care products, growth factors, hormones, vitamins, trace elements, fats, acids, bases, bleaches, varnishes, alcohols, proteins, enzymes, nucleic acids, hydrogels, detergents, surfactants, alcohols, proteins, fluorescent substances or the like or combinations of the foregoing.

Thereby, the adhesives can be thermosetting polymers, thermoplastics or elastomers. The adhesives can be cured chemically, as in the case of acrylates (such as cyanoacrylate, methyl methacrylate, unsaturated polyesters, anaerobically curing adhesives, radiation-curing adhesives). If necessary, curing can be carried out by means of polyaddition, as in the case for epoxy adhesives, polyurethane adhesives and silicones. Curing can also occur via a polycondensation reaction as in phenolic resins, polyimides, polysulfides, bismaleinides, silane-modified polymers, and also silicones. Physically curing adhesives such as solvent-based adhesives, diffusion adhesives, contact adhesives, water-based dispersion adhesives, and colloidal systems can be used. It is also conceivable that hotmelt adhesives and plastisols are used.

Furthermore, it is also conceivable that the first substance portions and the second substance portions differ in that the first substance portions are linked or linkable to a larger number of substance portions than the second substance portions or vice versa. This allows to adjusted the concentration and/or volume ratio and the relative ratio of the substances to each other. The functional groups can be formed homogeneously or heterogeneously. It is conceivable, for example, that a substance and the associated functional groups are heterogeneous, i.e. that different functional groups can be used. This is desirable, for example, if it is desired that, for example, certain linkers are first provided with protection groups during preparation and are to be used for certain bonds, for example first substance to first substance or second substance to second substance or also first substance to second substance. It is also conceivable that a first functional group enables bonding of two capsules, and a second, different functional group enables bonding of capsules on surfaces or fibers. It is also conceivable that a first functional group enables bonding of two capsules, and a second, different functional group enables changing the properties of the capsules, e.g. biocompatiblity, solubility, or similar properties. It is also conceivable that heterogeneous functional groups make it possible to form a three- or multi-component system.

Further, a first functional group can be adhered to the surface with the first substance portion; or in other words, it can be provided that the first substance portion adheres to the surface via the first functional group.

However, it is also conceivable that all functional groups are formed homogeneously, i.e. Identically. In the case of heterogeneous formation, it is also conceivable that this is combined with further properties or differences in the design of the linkers (e.g. length, angle, type of linker, etc.).

The first substance portions can have an essentially identical size and/or the second substance portions can have an essentially identical size. The size can mean in particular the spatial extent, but also the mass or the occupied volume. It is conceivable that the first substance portions and the second substance portions each have an identical size or quantity.

In particular, however, it is also conceivable that the first substance portions and the second substance portions have different sizes.

The choice of size also determines the respective (local) volume and/or the respective local concentration of the respective substance.

The multi-component system can have a (network) structure with interspaces, the (network) structure being formed by substance portions of the first substance, an environmental medium being arranged in the interspaces and at least one substance portion of the second substance being arranged at least in sections. The result is improved mixing of the individual substances and thus also improved substances usage.

Furthermore, it can be provided that a substance portion of the first substance and/or the second substance is arranged in a capsule, in particular a nanocapsule and/or microcapsule. The encapsulation makes it easy to provide a defined mass or a defined volume of the first and/or second substance for the multi-component system.

In a multi-capsule system or, for example, a two-component capsule system (2C capsule system), it is possible for the capsule contents to be bound to one another in a defined number and/or a defined ratio and spacing in separate spaces until the capsules are activated and thus their contents can react with one another or are forced to react with one another or mix if the capsules have the same contents. One substance portion of a substance is arranged in or enclosed in one capsule. It is also conceivable that a capsule contains multiple substance portions. An arrangement of capsules with first substances and second substances can also be called a capsule complex and has a function similar to a (mini) reaction flask, in which the reagents are mixed with each other after activation at a defined time point and the reaction of the substances with each other is initiated. Due to the large number of these capsule complexes, the mode of action is summed up and there is a greater effect or the mixing and reaction of the substances is improved. Further advantages result from the better mixing or the individual substances and reaction components with each other, and thus—compared to previous systems—a higher turnover can be achieved with lower substance usage. In the case of a single-component system, mixing can be significantly improved. Particularly in the case of high-viscosity adhesive tapes, a one-component adhesive can achieve complete crosslinking through the adhesive tape.

In particular, it can be provided that a capsule for the first substance has a different size than a capsule for the second substance, especially wherein the capsule for the first substance is larger than the capsule for the second substance. This results in an adjustment of the ratio of the volumes of the first substance in relation to the second substance (or vice versa) and also an adjustment of the activation behavior.

The multi-component system according to the invention comprises a first substance N1 and a second substance N2, wherein the first substance N1 is comprised in at least one capsule K1 and the second substance N2 is comprised in at least one capsule K2, and the at least one capsules K1 and K2 are optionally linked to each other.

Thereby, the optional linkage between the capsules K1 and K2 can be a direct linkage.

The linkage between both capsules K1 and K2 can also be a bridge, wherein the bridge is formed by the linkage of at least a first linker arranged on one of the capsules. However, the capsules can also have two inkers, wherein the first linker L1 is arranged on the capsule K1 and the second linker L2 is arranged on the capsule K2. Functional groups can be arranged on these linkers, which enable the two capsules to be linked via the linkers by specific reaction.

The linkage between the two capsules, either directly or via the bridge (i.e. by means of the linkers and the functional groups) is, in a preferred embodiment, a covalent bond.

A direct linkage between the two capsules can be any direct (chemical, biological or mechanical) linkage.

The material of the linkers of the capsules is selected from the group consisting of co-polymers, star polymers, alkanes (in particular ($C_1$-$C_{20}$)alkanes), cycloalkanes (in particular ($C_3$-$C_{12}$)cycloalkanes), alkenes (in particular ($C_2$-$C_{20}$)alkenes), alkynes (in particular ($C_2$-$C_{20}$)alkynes), biopolymers, proteins, silk, polysaccarides, cellulose and its derivatives, starch, chitin, nucleic acids, DNA, DNA fragments, synthetic polymers, homopolymers, polyethylenes, polypropylenes, polyvinyl chloride, polylactam, natural rubber, polyisoprene, copolymers, random copolymers, gradient copolymer, altemating copolymers, block copolymers, graft copolymers, arcylnitrile butadiene styrene (ABS), styrene acrylonitrile (SAN), butyl rubber, polymer blends, polymer alloy, inorganic polymers, polysiloxanes, polyphophazenes, polysilazanes, ceramics, basalt, isotactic polymers, syndiodactic polymers, atactic polymers, linear polymers, crosslinked polymers, elastomers, thermoplastic elastomers, thermosetting polymers, seml-crystaline linkers, thermoplastics, cis-trans polymers, conductive polymers, supramolecular polymers, combinations thereof, or any other type of linkage of the capsule to a functional group.

The functional groups arranged on the capsules via the linkers are selected from the group consisting of alkanes (in particular ($C_1$-$C_{20}$)alkanes), cycloalkanes (in particular ($C_3$-$C_{12}$)cycloalkanes), alkenes (in particular ($C_2$-$C_{20}$)alkenes), alkynes (in particular ($C_2$-$C_{20}$)alkynes), phenyl substituents, benzyl substituents, vinyl, allyl, carbenes, alkyl halides, phenol, ethers, epoxides, ethers, peroxides, ozonides, aldehydes, hydrates, imines, oximes, hydrazones, Semicarbazones, hemiacetals, hemiketals, lactols, acetal/ketal, aminals, carboxylic acid, carboxylic acid esters, lactones, orthoesters, anhydrides, imides, carboxylic acid halides, carboxylic acid derivatives, amides, lactams, peroxyacids, nitriles, carbamates, Hernstoff, guanidines, carbodiimides, amines, aniline, hydroxylamines, hydrazines, hydrazones, azo compounds, nitro compounds, thiols, mercaptans, sulfides, phosphines, P-Ylene, P-Ylides, biotin, streptavidin, metallocenes, or the like.

In one embodiment, the multi-component system of the present invention comprises a linkage of the capsule K1 to the capsule K2.

However, more than one capsule K2 can also be linked to the capsule K1. Depending on the size of the capsule K1, up to 50, up to 40, up to 30, up to 20, or up to 10 capsules K2 are linkable to the capsule K1. This can, for example, enable the formation of three-dimensional structures. Furthermore, it is possible to control the amounts of the respective substances present via the ratio of the number of capsules and thus to favor a desired stoichiometric ratio. In some embodiments, it is preferred that one capsule K1 is associated with 2, 3, 4 or 5 capsules K2.

The capsules of the system according to the invention have at least one shell.

In some embodiments, the capsules can have more than one shell. For example, in such embodiments, the capsules have 2, 3, 4, 5, 6, 7, 8, 9, or 10 shells.

The shells are applied using known techniques. For example, further shells can be applied to a first shell using spray drying processes. This process can be repeated as often as required. Different materials can also be used for the shells in order to tailor the properties of the shells.

For example, the materials used for the shell or the number of shells can change, e.g., the time it takes for the substance contained in the core of the capsule to be made accessible.

If the number of shells in one capsule is increased compared to another capsule, the substance or the substance portion from the capsule with the lower number or capsules will be accessible first when the capsule is activated by suitable mechanisms. The time between making the substances of the respective capsules accessible can therefore be adjusted by the number of shells.

The properties of the shell can also be adjusted by the materials used. For example, the choice of suitable polymers and copolymers can adjust the hydrophilicity or hydrophobicity of the shell and thus influence, for example, the release of the substance in a suitable environment.

Also, the degree of crosslinking of polymers or copolymers can be used to tailor the activation of the capsules. For example, methacrylates (such as methyl methacrylate, MMA) can be crosslinked to polymethacrylates using UV radiation. In this process, UV radiation is applied for a shorter time in the production of a first material than in the production of a second material. The second material has a higher degree of crosslinking than the first material due to the longer irradiation. If activation of the capsules made from these materials is then triggered by means of a (linear) temperature rise, the capsule with the lower degree of crosslinking will first release the contained substance. In one embodiment, the multi-component system according to the invention comprises capsules K1 and K2, each comprising an at least partially crosslinked (co)polymer which has a different degree of crosslinking in the respective capsules K1 and K2.

Likewise, the choice of different (co)polymers can change the release properties of the shell. Therefore, one embodiment has capsules for the production of which different (co)polymers were used.

The preparation of the shell of the capsules can comprise at least one polymer, copolymer, wax, resin, protein, polysaccharide, gum arabic, maltodextrin, inulin, metal, alloys, ceramics, acrylate polymer, microgel, phase exchange material, lipids, maleic formaldehydes, resins, carbohydrates, proteins, phase exchange material, and/or one or more other substances or combinations thereof.

The activation of the capsules of the multi-component system is achieved by methods known to the skilled person. Thereby, different capsules can be activated either by the same mechanism or by different mechanisms.

Common mechanisms for activating the multi-component system capsule(s) include changing pressure, pH, UV radiation, osmosis, temperature change, light, humidity change, addition of water, ultrasound, enzymes, diffusion, dissolution, degradation control, erosion, or the like.

One embodiment of the present invention requires that at least one of the capsules of the multi-component system can be activated by a different mechanism than the other capsules. For example, in a multi-component system, the capsules K1 and K2 can be activated by a different mechanism than the other capsules, such as K3, of the multi-component system.

In a multi-component system, for example, one capsule (e.g. K1) can be activated at one temperature T1, while another capsule (e.g. K2) is activated at a different temperature T2. For example, the activation of the capsules can be controlled by the respective environmental temperature.

It is also conceivable, for example, that one capsule is activated by UV radiation, while the activation of a second capsule takes place via a change in pH.

By selecting the materials, such as suitable polymers, for the shell, the release of the substance in the capsule can be controlled in a targeted manner. In this way, the activation times of the respective capsules can be set in the range from a few seconds to several days.

It is also conceivable that the capsules of the first substance have an identical size. This also serves to adjust the activation behavior or the mixing behavior.

The capsules can, for example, be applied to a surface to be bonded, for example to a metal surface, as a pre-applicable adhesive, for example by a dispensing and/or spraying process. Metal surfaces usually oxidize within about 15 minutes. An oxide layer is formed. This oxide layer has a negative effect on bonding of the metal surface. For this reason, a metal surface must normally be processed again before bonding with another surface (with a metal or another material) can take place. There is then a time window for bonding of approx. 15 min until the oxidation layer forms again.

The pre-applicable multi-component system of the present invention prevents the formation of the oxide layer on the metal surface. The surface is then protected from oxidation by the microcapsules, if necessary also by the dispersion medium (matrix). This results in the advantage that process steps can be omitted (repeated processing of the metal surface to remove the oxidation layer). In addition, this adhesive application enables the preparation steps (manufacture of a metal part and bonding) to be designed much more flexibly. Irrespective of the small time window between surface processing and bonding. Since bonding is independent of the formation of the oxide layer after surface treatment, bonding can be performed under more reproducible conditions, which also results in an increase in the quality of the bonding.

The pre-applicable adhesive can be applied in the form of microcapsules (without linkage) with a first substance and further microcapsules (without linkage) with a second substance. In addition, the application can also be in the form of single, double or multi-component microcapsules or in combination thereof. In this case, the capsules with the first adhesive component are in a defined volume ratio to the capsules with the second adhesive component. Linking or capsules with the first adhesive component and the second adhesive component can be achieved by interaction. In particular weak interaction, and/or by covalent bonding. The multi-component system of the present invention comprises a substance N1 comprising an adhesive or a component of a multi-component adhesive in a capsule K1. In one embodiment, a one-component adhesive is pre-applied to a surface or material in at least one capsule (microcapsule), wherein the capsule(s) of the first substance can be embedded in an environmental matrix.

In one embodiment, the multi-component system is a two-component adhesive system. Thereby, the substances of the multi-component adhesive system can be selected from the group consisting of epoxy adhesives, polyurethanes, fibrin adhesives and combinations thereof. Preferably, the multi-component adhesive system comprises an epoxy adhesive or polyurethane adhesive.

In one embodiment, the multi-component system comprises an epoxy adhesive, wherein the substance N1 in the capsule K1 comprises a resin of an epoxy adhesive, and the resin is preferably selected from the group consisting of glycidyl-based epoxy resins, bisphenol-based epoxy resins (such as bisphenol-A, bisphenol-B, bisphenol-F, bisphenol-S, bisphenol-F epichlorohydrin resin having an average molecular weight of <700, or bisphenol-A epichlorohydrin resin having an average molecular weight of <700), novolak epoxy resins, aliphatic epoxy resins, and halogenated epoxy resins. The substance N2 is in capsule K2 and comprises a curing agent of an epoxy adhesive, wherein the curing agent is preferably selected from the group consisting of amines, such as polyvalent amines, aliphatic amines, amides, carboxylic anhydrides, mercaptans, dicyandiamide, polyethylene, triethylenetetraamanine, N'-(3-aminopropyl)-N,N-dimethylpropane-1,3-diamine and dicarboxylic anhydrides.

In certain embodiments, the quantitative ratio of substances N1 to N2 in the multi-component system can be in the range of about 0.25 to about 4, about 0.5 to about 2, preferably about 0.7 to about 1.3, more preferably about 0.8 to about 1.2, and more preferably in the range of about 0.9 to about 1.1, most preferably about 1.

In certain embodiments of the invention, the ratio between the diameters of the capsules K1 and K2 in the multi-component system is in the range of about 0.5 to about 2, about 0.5 to about 2, preferably about 0.7 to about 1.3, more preferably about 0.8 to about 1.2, and more preferably in the range of about 0.9 to about 1.1, most preferably about 1. Typically, the diameters of the capsules are determined by light microscopic methods.

In order to obtain the most uniform possible adhesive behavior over a surface, it is advantageous if the size (and thus also the diameter) of the capsules of a substance are largely uniform. Preferably, the size distributions of the capsules of a substance (i.e. of the capsules K1, K2, etc.) are monodisperse. In preferred embodiments, the diameter of the capsules of a substance in a range of the diameter of the maximum of the size distribution of the respective capsule is ±50% of the diameter of the maximum. If the maximum of the diameter of the size distribution of a capsule is 50 μm, about 90% of the capsules should be in a diameter range of from 25 μm to 75 μm.

In certain embodiments, the capsules of the multi-component system, preferably the capsules of a system comprising an epoxy adhesive, have a diameter in the range from about 10 μm to about 400 μm, preferably 10 μm to about 200 μm, preferably 40 μm to 120 μm, more preferably 40 μm to 80 μm. The diameter of the second capsule of such a system is in the range of about 2 μm to about 30 μm, preferably 10 μm to 25 μm, more preferably 10 μm to 20 μm. The diameter of the capsules is determined by optical methods such as microscopy.

The multi-component system of the invention can further comprise additional substances. In one embodiment, the system according to the invention comprises at least one further substance N3 arranged in at least one third capsule K3.

This third capsule K3 is typically not linked to one of the first capsules K1 or one of the second capsules K2. That is, in a preferred embodiment, the multi-component system comprises a three-component system, wherein the first capsule K1 comprising the first substance N1 and the second capsule K2 comprising the second substance N2 are linked to each other, while the capsule K3 is not linked to either capsules K1 and/or K2.

It is also conceivable that the capsule K3 can be bound to at least one of the capsules K1 and/or K2.

The substance N3 contained in the third capsule K3 can be, for example, an adhesive, a sealant, fragrances, colorants, fillers, care products, growth factors, hormones, vitamins. trace elements, fats, acids, bases, bleaches, vanishes, alcohols, proteins, enzymes, nucleic acids, hydrogels, detergents, alcohols, surfactants, proteins, fluorescent substances and/or dyes or the like, or combinations thereof.

When substance N3 is selected as an adhesive, the adhesive can be selected from the group consisting of epoxy adhesives, silicone adhesives, polyurethane adhesives, acrylic adhesives, fibrin adhesives, phase change materials, and combinations thereof.

In one embodiment, the substance N3 in the third capsule K3 can comprise a silicone or a silicone adhesive.

In addition to its function as an adhesive, the silicone can also have a sealing effect.

Suitable combinations or substances in the various capsules of the multi-component system allow the various desired properties to be specifically adjusted. e.g. the adhesion and sealing properties of the multi-component system can be adjusted by the choice of substances.

In a preferred embodiment, the multi-component system comprises a substance N1 in a capsule K1 comprising a first component of a multi-component adhesive, a substance N2 in a capsule K2 comprising a second component of a multi-component adhesive and a substance N3 in capsule K3, wherein the substance in capsule K34 is selected from the group consisting of silicone adhesives, polyurethane adhesives, acrylic adhesives, fibrin adhesives, phase change materials, sealants, and combinations thereof. In one embodiment, substance N1 comprises a resin of an epoxy adhesive, substance N2 comprises a curing agent of an epoxy adhesive, and substance N3 comprises a silicone, silicone adhesive, or polyurethane adhesive. The two capsules comprising the components of the epoxy adhesive are covalently bonded to the capsule K2 via a bridge.

As described above, the properties of the system can be varied via the ratio of the amounts of the components of the multi-component system. The following ratios of silicone to epoxy adhesive or polyurethane adhesive to epoxy adhesive of about 1:9 to about 9:1, preferably about 1:5 to 5:1, more preferably about 1:1, have proven suitable for various applications.

In one embodiment, a two-component adhesive (e.g. epoxy adhesive) is pre-applied. The first component of the epoxy adhesive is contained in at least one first capsule (microcapsule) and the second component of the epoxy adhesive is contained in at least one second capsule (microcapsule). Alternatively or additionally, the capsules can be incorporated in an environmental matrix.

In one embodiment, a microencapsulated epoxy adhesive (two-component adhesive, first and second component) is pre-applied with a silicone adhesive (one-component adhesive, third component). The first component of the epoxy adhesive is contained in at least one first substance portion (microcapsule) and the second component of the epoxy adhesive is contained in at least one second substance portion (microcapsule), wherein two of the three components can be linked to one another. Preferably, the microcapsules of the epoxy adhesive are linked to one another. Alternatively or additionally, the substance portions may be incorporated in an environmental matrix.

In one embodiment, a microencapsulated epoxy adhesive (two-component adhesive, first and second component) is pre-applied with a polyurethane adhesive (one-component adhesive, third component). The first component of the epoxy adhesive is contained in at least one first substance portion (microcapsule) and the second component of the epoxy adhesive is contained in at least one second substance portion (microcapsule), wherein the two components can be linked to one another. Preferably, the microcapsules of the epoxy adhesive are linked to one another. In addition, the polyurethane adhesive is contained in at least one third substance portion (microcapsule).

In a two-component polyurethane adhesive, the first component of the polyurethane adhesive is in at least one substance portion (microcapsule) and the second component of the polyurethane adhesive is in at least one fourth substance portion (microcapsule). Preferably, the two microcapsules filled with the respective components of the polyurethane adhesive are inked to one another. Alternatively or additionally, the substance portions can be incorporated in an environmental matrix.

In one embodiment, the capsules are embedded in an environmental matrix. The environmental matrix allows easy application of the capsules and further protects the metal surface from oxidation. The matrix can be a solvent such as water, acetone, or ethanol, another adhesive, a polymer, an antibiotic solution, an antimicrobial solution, a grease, a paste, or the like.

A further task of the present invention is to further improve a multi-component system, in particular in that the metering of individual components of a multi-component system and their mixing can be better controlled, thus improving the efficiency of the reaction of the multi-component system.

Conceivably, activation of the capsules of the multi-component system is accomplished by at least one change in pressure, pH, UV radiation, osmosis, temperature, light intensity, humidity, or the like.

It is conceivable to use one or more activation mechanisms in parallel and/or sequentially. The sequential opening mechanism can be implemented, for example, by a different thickness of the shell, different shell material, different capsule size or the like.

Possible capsule types include, for example, single capsules, double capsules, multi-core capsules, capsules with cationic or anionic character, capsules with different shell material, granules, capsules with multiple shells, capsules with multiple layers or shell material (so-called multilayer microcapsules), capsules with metal nanoparticles, matrix capsules and/or hollow capsules, capsules with a dense shell material, e.g., an absolutely dense shell material with a dense shell material, porous capsules and/or empty porous capsules (e.g. to encapsulate odors).

The first substance and the second substance can be components of a multi-component adhesive, in particular a two-component adhesive.

In principle, other fields of application are also possible.

In particular, it can be provided that the first substance and the second substance are components of a one-component adhesive. In other words, the first substance and the second substance can be the same substance.

For example, the first and second substances can be different adhesives.

The capsules are formed or functionalized with linkers and with functional groups.

The linkers are intended to crosslink the capsules with one another. It can be provided that the functional groups are still provided with a protection group. The distance between the capsules can be determined by the length of the linkers. The length of the linkers should be chosen so that the radius of the contents of the discharged liquid of the capsules slightly overlaps with the contents of the adjacent capsules to ensure linking. For a higher viscosity environmental medium (such as an adhesive tape), the length of the linkers should be smaller than for a lower viscosity medium such as a paste or liquid.

In general, intra-cross-linking of capsules is possible. Here, capsules of one capsule population are crosslinked to one another.

In general, it is possible to crosslink capsules with the same content via intra-cross-linking.

In general, inter-crosslinking of capsules is possible as an alternative or in addition. Here, capsules of at least two different capsule populations are crosslinked with one another.

In general, it is possible that capsules with different contents are linked via inter-linking.

It is conceivable that in the case of chemically curing adhesives, resin and hardener are present in the two-component system with two separate reaction chambers in a defined volume ratio in separate capsules and are protected against the activation reactions under storage conditions. The curing reaction is then triggered by, for example, changes in pressure, pH, UV radiation, osmosis, temperature, light intensity, humidity or the exclusion of air.

The capsules of a single-component capsule system or multi-component capsule system, e.g. a two-component capsule system, can be introduced into the gas phase, into a pasty medium, into a viscous medium, into a high-viscosity medium, into a liquid systems and/or applied on solid surfaces.

It is conceivable, for example, that the capsules are contained in a spray (spray adhesive).

It is conceivable that a multi-component system, e.g. a two-component adhesive, is incorporated in a pasty medium as the environmental matrix. This makes it possible to apply the adhesive very precisely to an area to be bonded, for example a surface. The two-component adhesive would not be activated until activation, and the process time and activation can be determined individually.

It is conceivable that the capsules are attached to a surface. e.g. a carrier material. The capsules can, for example, be contained in and/or on a double-sided or single-sided carrier material.

The carrier material can comprise, for example, a surface, a plastic, a plastic film or a metal or a metal foil or a plastic foam or a textile fabric or a paper or wood or a fiber composite material. It is also possible that the carrier material is further processed, for example by printing or die cutting, or otherwise.

It is conceivable that the substance portions (also without encapsulation) are attachable, or are applicable, or are applied, or are attached to a surface, e.g. a carrier material. For example, application in the form of dots, as well as geometric or non-geometric shapes formed from dots, stripes, spheres, ellipses, lines, tracks, etc. is possible.

In particular, it is also conceivable that the arrangement of the one or more substance portions of a first substance and the arrangement of the one or more substance portions of at least a second substance on a surface, in particular during activation, e.g. by pressure, temperature, induction, e.g. when bonding the surface to another surface, can be used to achieve a mixing of the substances, in particular an optimal mixing of the substances, and thus a combination of two different properties and thus a desired property of the resulting hybrid substance can be achieved. In one embodiment, a hybrid adhesive with improved adhesion compared to the individual adhesive components is obtained by applying one or more substance portions of a first adhesive and one or more substance portions of a second adhesive to a surface to be bonded, wherein the volume of the one or more substance portions of the first substance is in a defined ratio to the volume of the one or more substance portions of the second substance, and the arrangement of the one or more substance portions of the first substance and the arrangement of the one or more substance portions of the second substance on the surface to be bonded is configured in that, when the surface is bonded to a further surface (pressure), mixing of the substances, in particular optimum mixing of the substances, is enabled in a defined mixing ratio.

One possible application of a double- or single-sided carrier material comprising the capsules of a single-component capsule system or multi-component capsule system. e.g. a two-component capsule system, is an adhesive tape and/or adhesive strip and/or adhesive label.

One possible application of a double- or single-sided carrier material containing the capsules of a single-component capsule system or multi-component capsule system. e.g. a two-component capsule system, is an adhesive tape and/or adhesive strip and/or adhesive label for covering wounds in humans or animals. Application to plants, e.g. trees, is also generally possible. The carrier material can be applied, for example, to the skin and/or body surface of the human or animal or plant. It is also possible that the carrier material is applied inside the body of the human or animal or plant.

In particular, this can enable covering wounds in humans, animals or plants. It is possible for wounds to be selectively bonded. It is then provided that a pressure-sensitive adhesive on a double-sided or single-sided carrier material enables initial adhesion for positioning of the carrier material. Bonding takes place via activation of the capsules, which enables final adhesion. Alternatively or additionally, the restoration of a tissue, e.g. bone and/or cartilage tissue, nerve tissue, muscle tissue, fatty tissue, epithelial tissue, enamel, dentin, pulp, parenchyma, kellenchyma, sclerencym, epidermis, periderm, xylem, phloem or organ, which has been damaged, e.g. by accident, injury, surgery or other causes, can be enabled by the application of a double-sided or single-sided carrier material of single- or multi-component adhesives.

Conceivably, a surface to be bonded is formed or provided with (i.e., functionalized with) a functional group complementary to a functional group with which two-component microcapsules have been functionalized. The two-component microcapsules can be linked to the surface to be bonded. Thus, the surface to be bonded can be formed non-tacky. The time point, as well as the type of activation of the two-component microcapsules can be precisely determined. This can find application, for example, in bonding in the micro-range, such as bonding electronics, displays, eyepieces, lenses or the like. It is also conceivable that it can be used in the area of deep soft tissue injuries in humans or animals. It is conceivable that deep and/or larger wounds can also be bonded using the process described. Minimally invasive bonding of deep and/or large wounds is conceivable. In general, bonding of human, animal or plant tissues and/or organs of any kind is conceivable.

In particular, it is conceivable that the capsules of a single-component capsule system or multi-component capsule system, e.g. a two-component capsule system, additionally or alternatively contain pharmacologically active substances, for example drugs including antibiotics, growth factors, disinfectants, or the like. This can, for example, enable better wound healing or adhesion of tissues or organs of all kinds.

For example, the substance N1 in the first capsule K1 may comprise a pharmaceutically active ingredient. In addition to the previously mentioned pharmaceutical active ingredients, the first substance can also contain, for example, an antiseptic, anti-inflammatory agents, growth factors, antibiotics or combinations thereof.

Suitable antiseptics include alcohols (such as ethanol, hexanol, n-propanol, or i-propanol or mixtures of the foregoing or mixtures of the foregoing with water), quaternary ammonium compounds (such as benzalkonium, benzethonium chloride, brilliant green, cetrimide, cetylpyridinium chloride, octenidine(dihydrochloride), polyhexanide), iodine-containing compounds (such as B povidone-iodine or tincture of iodine), halogenated compounds (such as triclosan, chlorhexidine, 2,4-dichlorobenzyl alcohol), quinoline derivatives (e.g. oxiquinoline), benzoquinone derivatives (e.g. ambazone), phenol derivatives (hexachlorophene) or mercury-containing compounds (e.g. merbromine or thiomersal).

In a further capsule of the multi-component system, an adhesive may be included, such as in the second capsule of the multi-component system K2. This adhesive may be selected as a compatible adhesive for use in or on the human or animal body. For example, the adhesive used is a fibrin adhesive.

It is also conceivable that the capsules of a single-component capsule system or multi-component capsule system. e.g. a two-component capsule system, are porous capsules. Porous capsules can be used to absorb liquids and/or odors. It is conceivable, for example, that porous capsules can be used to absorb wound fluid from wounds of animals, humans, or even plants.

It is also possible that a selected release profile is achieved via the capsules of a multi-component capsule system. e.g. a two-component capsule system. For example, a gradual and/or delayed release of drugs or growth factors and/or active ingredients of aN kinds is conceivable.

In one embodiment, for example, one capsule of the multi-component system can comprise a pharmaceutically active ingredient, such as an antiseptic, and the second capsule can comprise an adhesive or a component of a multi-component adhesive (e.g. a fibrin adhesive). The activation of the capsules can be timed so that, for example, the pharmaceutically active ingredient is first released by activating the capsule. In this way, a wound could be treated with an antiseptic to prevent the threat of sepsis. After a defined period of time, the capsule comprising the adhesive could then be activated, thus ensuring that the wound is bonded or closed.

The capsules of the multi-component system according to the invention can be activated by different mechanisms. It is conceivable that one or more capsules are activated by the same mechanism (e.g. capsule K1 and K2), while at least one of the remaining capsules can be activated by a different mechanism. That is, in such an embodiment, at least one of the capsules of the multi-component system according to the invention could be activated differently from the other capsules.

Activation of the at least one capsule (e.g., K1, K2, and/or K3) can be achieved by change in pressure, pH. UV radiation, osmosis, temperature change, light, change in humidity, addition of water, ultrasound, by enzymes, by diffusion, by dissolution of the capsule, degradation control, erosion, or the like.

However, it is also conceivable that a targeted activation of the different capsules is controlled by the different number of shells in the respective capsule.

Alternatively, the activation can also be controlled via different shell materials. For example, different (co)polymers, which have different hydrophilicities, can be used in the different shells of the capsules. Thus, a desired activation behavior can be tailored by the ratio of hydrophilic and hydrophobic monomer building blocks. It is also possible for a desired (temporally) staggered activation to occur via the different crosslinking of a (co)polymer. For example, methacrylates such as methyl methacrylate (MMA) can be crosslinked by UV radiation. The degree of crosslinking of the poly(methy)methacrylate (PMMA) can be specifically controlled via the duration of the UV radiation. The release or activation of the capsule then takes place overtime depending on the degree of crosslinking of the (co)polymer used in the capsule shell.

It is conceivable that in a two-component capsule system for faster healing of a wound, a first capsule population with fibrin is activated immediately, but a second capsule population with antibiotics has a prolonged activation mechanism so that antibiotic release is delayed compared to fibrin release. In addition, it would be possible to insert an empty, porous capsule that absorbs odors and/or wound fluid.

It is conceivable that a two-component microcapsule system contains a first capsule population with an aqueous component (first phase) and a second capsule population with an oil-containing component (second phase). Conceivably, a two-component microcapsule system thus enables the aqueous component and the oil-containing component, i.e., the first phase and the second phase, to be brought into solution in a defined ratio. Conceivably, a two-phase product based on a two-component microcapsule system with a defined ratio (of first phase to second phase) can thus be obtained. For example, it is conceivable that a two-phase product based on a two-component microcapsule system can be applied to a tissue/fiber in a defined ratio. Conceivably, a two-phase product based on a two-component microcapsule system can prevent substances from drying out and allow them to be stored in a common packaging. In general, such a system can be used for reactions to take place more effectively than with conventional systems.

It is also conceivable that two capsule populations of a two-component capsule system with the same content but with different activation mechanisms are linked to one another by intra-crosslinking on a carrier material in a batch process. This can allow a longer lasting release of e.g. pharmacologically active substances compared to a one-component capsule system.

It is also conceivable that in a two-component capsule system, unstable substances are stored for longer in their more stable form in the environmental medium by encapsulation. Only when the capsules are activated can the stable component in the first capsule react with the activator from the second capsule and be converted into the reactive form.

Another possible application of a double- or single-sided carrier material containing the capsules is an adhesive tape and/or adhesive strips in the field of personal care, in the manufacture or repair of clothing and/or shoes, in the construction or handicraft sector, in DIY, carpentry, in the automotive industry, adhesive technology, electrical industry or the like.

It is also conceivable that the capsules of the one-component capsule system and/or the two-component capsule system are applied in the field of care products for humans, animals, plants or objects.

It is conceivable that a mufti-component system, for example a two-component system, can also be used for self-healing products.

It is possible that a monomer is encapsulated in a first capsule and an activator is encapsulated in another capsule. Targeted activation allows a capsule complex to react with the environmental matrix.

It is conceivable, for example, that capsules of a two-component system are introduced into paper. Sugar monomers can be encapsulated in the first capsule population, and a corresponding activating enzyme in the second capsule population. Activation can cause the capsules to burst, and the activating enzyme can bind the sugar monomers to the fibers of the paper. It is conceivable that one or more breaks can be repaired in this way. It is conceivable that this principle could be applied to fibers of any kind, for example plastic fibers.

Generally, monomers can be present in a first capsule population, and an initiator for polymerization of the monomers in the first capsule population can be present in another capsule population.

This principle can be applied to monomers of all types.

In general, two monomers can also be present in different capsules.

For example, the carboxylic acid can be present in a first capsule and the diol in a second capsule. By activating the capsules, the polycondensation can be activated and the two monomers react to form a polyester.

In general, a three-capsule system is also conceivable. The first and second capsules can each contain the same or different monomers. The third capsule can contain an initiator.

For example, the polycondensation of phenoplast would be possible, with the phenol in one capsule and the aldehyde in another capsule. The initiator is present in the third capsule.

In general, this principle can be applied to any polymerization.

It is possible that the capsules contain, at least in part, one or more fragrances, colorants, fillers, care products, growth factors, hormones, vitamins, trace elements, fats, acids, bases, bleaching agents, alcohols, proteins, enzymes, nucleic acids, hydrogels or the like.

It is also conceivable that the capsules of the one-component capsule system or the two-component capsule system are used in the field of cleaning agents. Accordingly, it is possible that the capsules at least partially contain one or more fragrances, dyes, detergents, surfactants, alcohols, acids, bases, bleaching agents, enzymes or the like.

It is also conceivable that the capsules of the one-component capsule system or the two-component capsule system are used in the field of diagnostic procedures. Accordingly, it is possible that the capsules at least partially contain contrast agents, fluorescent substances and/or dyes.

It is also conceivable that the capsules of the one-component capsule system or the two-component capsule system (or generally of a mufti-component capsule system) are used in the field of detergents. Accordingly, it is possible that the capsules at least partially contain one or more fragrances, dyes, detergents, surfactants, alcohols, acids, bases, bleaching agents, enzymes or the like.

It is also conceivable that the capsules of the one-component capsule system or the two-component capsule system (or generally of a mufti-component capsule system) are used in the field of paints and coatings. Accordingly, it is possible that the capsules at least partially contain one or more epoxides, silicones, pigments or the like.

In particular, it is conceivable that homogeneously and/or heterogeneously functionalized capsule populations of a two-component capsule system are covalently linked to one another. In particular, it is conceivable that homogeneous and/or heterogeneously functionalized capsule populations of a two-component capsule system are covalently linked to one another by intra-crosslinking and/or inter-crosslinking. Both capsule populations can each be filled with different substances, e.g. different dyes. It is conceivable that one capsule population discharges at a particular event by a particular activation mechanism, and the other capsule population discharges at a second particular event by a particular activation mechanism. When both events occur, the two capsule contents mix, resulting in a particular color.

It is also conceivable that a carrier material is formed with at least one functional group to enable attachment to a surface of functionalized capsules.

In particular, it is conceivable that at least one area of a surface to be bonded is formed with functional groups. In addition, capsules of a single-component capsule system and multi-component capsule system can be formed with functional groups as described above.

Subsequently, the capsules are covalently linked to the functionalized surface by crosslinking. Activation of the capsules causes adhesive to be discharged and/or intermixed, resulting in the development of adhesive properties.

In addition, the surface of the carrier material of an adhesive tape can be functionalized. The single- and multi-component systems are mixed into the pressure-sensitive adhesive. In the next step, part of the capsule complexes is bound to the surface of the carrier material.

In another embodiment, the capsule complexes can be applied to all or portions of the surface of the pressure sensitive adhesive.

It is generally possible to produce the capsules by solvent evaporation, thermogelling, gelation, interfacial polycondensation, polymerization, spray drying, fluidized bed, droplet freezing, extrusion, supercritical fluid, coacervation, air suspension, pan coating, co-extrusion, solvent extraction, molecular incorporation, spray crystallization, phase separation, emulsion, in situ polymerization, insolubility, interfacial deposition, emulsification with a nanomole sieve, ionotropic gelation method, coacervation phase separation, matrix polymerization, interfacial crosslinking, congealing method, centrifugation extrusion, and/or one or more other methods.

It is generally possible to produce capsules by physical methods, chemical methods, physiochemical methods and/or similar methods.

It is generally possible for the shell of the capsules to comprise at least one polymer, wax resin, protein, lipids, maleic formaldehydes, resins, carbohydrates, proteins, polysaccharide, gum arabic, maltodextrin, inulin, metal, ceramic, acrylate, microgel, phase change material, and/or one or more other substances, as well as combinations thereof.

It is generally possible that the shell of the capsules is non-porous or not entirely porous. It is generally possible that the shell of the capsules is almost completely impermeable or completely impermeable.

It is generally possible that the substance in the capsules is solid, liquid and/or gaseous. In addition, it is possible that the core of the capsules comprises at least one phase change material, enzyme, carotenoid, living cell, at least one phenolic compound, or the like.

It is generally possible for the capsules to be formed with linear polymers, polymers with multivalence, star-shaped polyethylene glycols, self-assembled monolayers (SAM), carbon nanotubes, ring-shaped polymers, dendrimers, ladder polymers, and/or the like.

Possible protection groups include acetyl, benzoyl, benzyl, β-methoxyethoxymethyl ether, methoxytriyl, 4-methoxyphenyl)diphenylmethyl, dimethoxytrityl, bis-(4-methoxyphenyl)phenylmethyl, methoxymethyl ether, p-methoxybenzyl ether, Methyl thiomethyl ether, pivaloyl, tetrahydrofuryl, tetrahydropyranyl, trityl, triphenyl methyl, silylether, tert-butyldimethylsilyl, tri-iso-propylsilyloxymethyl, triisopropylsilyl, methyl ether, ethoxyethyl ether, p-Methoxybenzylcarbonyl, tert-butyloxycarbonyl, 9-fluorenylmethyloxycarbonyl, carbamates, p-methoxybenzyl, 3,4-dimethoxybenzyl, p-methoxyphenyl, one or more tosyl or nosyl groups, methyl esters, benzyl esters, tert-butyl esters, 2,6-di-substituted phenol esters (e.g., 2,6-dimethylphenol, 2,6-dilsopropylphenol, 2,6-di-tert-butylphenol), silyl esters, orthoesters, oxazoline, and/or the like.

Possible materials for coating the capsules include albumin, gelatin, collagen, agarose, chitosan, starch, carrageenan, polystarch, polydextran, lactides, glycolides and co-polymers, polyalkylcyanoacrylate, polyanhydride, polyethyl methacrylate, acrolein, glycidyl methacrylate, epoxy polymers, gum arabic, polyviyl alcohol, methyl cellulose, Carboxymethyl cellulose, Hydroxyethyl cellulose, Arabinogalactan, Polyacrylic acid, Ethyl cellulose, Polyethylene polymethacrylate, Polyamide (nylon), Polyethylene vinyl acetate, Cellulose nitrate. Silicones, Poly(lactide-co-glycolide), kerosene, caranuba, spermaceti, beeswax, stearic acid, stearyl alcohols, glyceryl stearate, shellac, cellulose acetate phthalate, zein, hydrogels or similar.

Possible functional groups include alkanes, cycloalkanes, alkenes, alkynes, phenyl substituents, benzyl substituents, vinyl, allyl, carbenes, alkyl halides, phenol, ethers, epoxides. Ethers, peroxides, ozonides, aldehydes, hydrates, imines, oximes, hydrazones, semicarbazones, hemiacetals, hemiketals, lactols, acetal/ketal, aminals, carboxylic acid, carboxylic acid esters, Lactones, Orthoesters, Anhydrides, Imides, Carboxylic acid halides, Carboxylic acid derivatives, Amides. Lactams, Peroxyacids, Nitriles, Carbamates, Hemstoff, Guanidines, Carbodlimides, Amines, Aniline, hydroxylamines, hydrazines, hydrazones, azo compounds, nitro compounds, thiols, mercaptans, sulfides, phosphines, P-Ylene, P-Ylides, biotin, streptavidin, metallocenes, or similar.

Possible release mechanisms (activation mechanisms) include diffusion, dissolution, degradation control, erosion, or similar.

It is conceivable that a combined release mechanism is present.

Possible linkers include biopolymers, proteins, silk, polysaccarides, cellulose, starch, chitin, nucleic acid, synthetic polymers, homopolymers, polyethylenes, polypropylenes, polyvinyl chloride, polylactam, Natural rubber, polyisoprene, copolymers, random copolymers, gradient copolymer, alternating copolymer, block copolymer, graft copolymers, arcylnitrile butadiene styrene (ABS), styrene acrylonitrile (SAN), Buthyl rubber, polymer blends, polymer alloy, inorganic polymers, polysiloxanes, polyphophazenes, polysilazanes, ceramics, basalt, isotactic polymers, syndiodactic polymers, atactic polymers, linear polymers, crosslinked polymers, elastomers, thermoplastic elastomers, thermosetting polymers, semi-crystalline inkers, thermoplastics, cis-trans polymers, conductive polymers, supramolecular polymers.

A inker can be any form of linkage between a capsule and a functional group.

Furthermore, the present invention relates to a method of preparing of a multi-component system. Accordingly, it is provided for a method of preparing a multi-component system with at least one first substance and at least one second substance, the first substance and the second substance being present in a plurality of substance portions, wherein the method comprises the steps of:

the first substance portions are formed with at least one first functional group, the second substance portions are formed with at least one second functional group, the first functional group reacts with the second functional group via a predefined interaction so that they are linked to one another.

In particular, it can be provided that the first substance portions are formed with at least one third functional group and are provided with a linker, the third functional groups each having at least one protection group, so that only correspondingly functionalized substance portions of the first substance can bind to the substance portions of the first substance, and wherein the method further comprises at least the step that the protection groups are initially present and are only removed when the first substance portions are to be linked to one another by means of the third functional groups. This prevents the substance portions, in particular capsules, of the first substance from already and preferably linking with further substance portions of the first substance. The protection groups can be removed after introduction into gas, low viscosity, liquid, high viscosity or solid phase, whereby the intra-crosslinking takes place.

The multi-component system can be a multi-component system as described above.

Possible areas of application of the method or system according to the invention include biotechnology, cosmetics, the pharmaceutical industry, the food industry, the chemical industry, agriculture, packaging technology, waste recycling, the textile industry, the manufacture of fiber composites, electrical engineering, mechanical engineering, medical technology, microtechnology, the automotive industry, paints, coatings, detergents, agrochemicals, solar cells, or the like.

Explicitly disclosed is thus the use of the method and/or system described above and also below for one of the following applications, alone or In combination, namely biotechnology, the pharmaceutical industry, cosmetics, the food industry, the chemical industry, agriculture, packaging technology, waste recycling, the textile industry, the manufacture of fiber composites, electrical engineering (e.g. In connection with the connection of electronic components, chip technology or the like), mechanical engineering, medical technology, microtechnology, the automotive industry, or the like. In particular, the following are mentioned in the cosmetics field:

In cosmetics, there are many two-phase or multi-phase products. Often there is an aqueous and an oily component. The 2C-microcapsule technology makes it possible to bring both phases into solution in a defined ratio.

In another embodiment, the two-phase products with the 2C-capsules can be applied to a cotton pad in a defined ratio. On the one hand, this would have the advantage that the substances do not dry out and can therefore be stored in normal packaging, and on the other hand, the efficiency with which the substances develop their effect is significantly increased with the same material input. The increase in efficiency of two substances can also be applied in creams, masks and so on.

In general, the principle of two-phase systems as described above can be applied to all multiphase systems.

In addition, the principle can generally be used to increase the yield of reactions and/or to make reactions more efficient.

In the area of product development, self-healing products would be conceivable, for example: The 2C-system can also be used for self-healing products. In one variant, the monomer is in one capsule and the activator or the second monomer is in the other capsule. Through targeted activation, the capsule complex reacts with the environmental matrix and bonds the fragments together.

For example, the capsules could be placed in paper. One capsule would contain sugar monomers and the other capsule would contain the corresponding enzyme. Activation, e.g. by UV radiation, would cause the capsules to burst, the enzyme would bind the corresponding sugar monomers to the fibers and the break would be repaired.

The same principle could also be applied to fibers, especially plastic fibers. The monomers would be present in one capsule, the initiator for polymerization in the other phase.

This principle can also be applied to paints, varnishes and many other materials. Further details and advantages of the invention will now be explained with reference to an example of an embodiment shown in more detail in the drawings.

Another aspect of the present invention is a method of bonding surfaces.

In this context, the method of bonding surfaces according to the invention comprises the following steps:

a) Providing at least one capsule K1, wherein the at least one capsule K1 comprises a substance N1, wherein the substance N1 comprises an adhesive or a component or a multi-component adhesive;
b) Optionally mixing of the at least one capsule K1 into an environmental medium;
c) Applying the capsule K1 to at least a portion of a surface of a first material;
d) Optionally drying the applied capsules;
e) Activating the capsule K1;
f) Adhering at least a portion of a surface of a second material to the at least a portion of the surface of the first material.

In this regard, the first material and the second material can be identical or different. The materials are preferably selected from the group consisting of metal, plastic, wood, paper, textile, fabric, yarn, fiber composite materials, mirrors, lenses, and combinations thereof.

The metals can in turn be selected from the group consisting of heavy metals, light metals, noble metals, semi-noble metals, alloys and base metals. Of particular interest to industry are bondings or aluminum or aluminum die casting.

In a preferred embodiment, the method according to the invention further comprises the following steps in addition to the method steps already described above:

(i) Providing at least one further capsule K2, wherein the at least one further capsule K2 comprises a substance N2, wherein the substance N2 comprises an adhesive or a component of a multi-component adhesive;
(ii) Applying the at least one capsule K2 to at least a portion of a surface of a first material;
(iii) Activate the at least one capsule K2.

It is preferred that the capsule K1 is linked to the at least one capsule K2, for example via a bridge. The linkage between the capsules K1 and K2 is preferably based on a covalent bond.

In one embodiment, the substance N1 in the at least one capsule K1 comprises an adhesive or a component of a multi-component adhesive, wherein the adhesive is preferably selected from the group consisting of epoxy adhesives, silicone adhesives, polyurethane adhesives, acrylate adhesives, fibrin adhesives, phase change materials, or combinations thereof.

In one embodiment, an epoxy adhesive is used in the method according to the invention. For this purpose, the substance N1 in the at least one capsule K1 comprises a component of an epoxy adhesive, preferably a resin of an epoxy adhesive. The substance N2 in the at least one capsule K2 also comprises a component of an epoxy adhesive, preferably a curing agent of an epoxy adhesive. Since the capsules K1 and K2 are preferably bonded to one another, the two components of this epoxy adhesive are already spatially arranged in such a way that they can react with one another in a targeted manner after activation of the capsules. The system described for the epoxy adhesive can easily be transferred to other multi-component adhesives. For example, the various components of a polyurethane adhesive can also be introduced into the capsules and activated after application to the surface of a first material.

In a further preferred embodiment, the method according to the invention can comprise additional method steps. Thus, a further substance N3 can be used in the method. Accordingly, the method comprises the following additional steps of (i) Providing at least one further capsule K3, wherein the at least one further capsule K3 comprises a substance N3, wherein the substance N3 comprises an adhesive or a component of a multi-component adhesive;

(ii) Applying the at least one capsule K3 to at least a portion of a surface of a first material;

(iii) Activating the at least one capsule K3;

The adhesive or multi-component adhesive component is in turn selected from the group consisting of epoxy adhesives, silicone adhesives, polyurethane adhesives, acrylic adhesives, fibrin adhesives, phase change materials, or combinations thereof.

The activation of capsule K3 can also be achieved by the mechanisms described above for the other capsules.

In one embodiment of the method according to the invention, the activation of the at least one capsule K1 is performed by a different mechanism than the activation of the at least one capsule K2 and/or the at least one capsule K3.

Thereby, it can be advantageous for the various capsules to be activated at the same time or at different time points. As already mentioned, it can be desirable, for example, that in wound care the wound is first treated with an antiseptic and that later activation of the adhesive ensures improved closure of the wound.

For example, in a method according to the invention in which a three-component system is used, the activation of the capsules K1, K2 and/or K3 at the following time points can be advantageous.

a) The activation of the at least one capsule K1 occurs at the same time or at a different time point than the activation of the at least one capsule K2;

b) In the case that the at least one capsule K1 and K2 are linked to each other, the activation of the at least one capsule K1 and K2 preferably occurs simultaneously;

c) In case the at least one capsule K3 is present, the activation of the at least one capsule K3 occurs at a different time point than the activation of the at least one capsule K1.

The multi-component system according to the invention can be extended as desired and can also comprise more than three different capsules, e.g. 4, 5, 8, 7, 8, 9, or 10 capsules.

If different capsules of a multi-component adhesive system, which are preferably also linked to one another, are to react with each other, these capsules are then also activated at the same time to enable such a reaction. By activating them at the same time, it can be ensured that the intended stoichiometry is maintained as well as possible during the reaction.

For example, if the capsules K1 and K2 contain different adhesives, it can be advantageous to activate them simultaneously or sequentially, depending on the system and application.

However, if the system used comprises, for example, a two-component adhesive system and an additional substance, it is typically advantageous for the two-component system to be activated at the same time, but not simultaneously with the additional adhesive system. This can be activated either upstream or downstream. Ideally, the time period between the activation of the different systems is selected so that the systems activated first have had time to react before the further system is activated.

A preferred embodiment of the method according to the invention comprises the following steps.

(i) Providing a first capsule K1 comprising a substance N1 and a second capsule K2 covalently linked to the first capsule K1 and comprising a substance N2, wherein a. the first substance N1 comprises a resin of an epoxy adhesive, and b. the second substance N2 comprises a curing agent of an epoxy adhesive;

(ii) Providing a capsule K3 comprising a further adhesive or sealing material, (iii) Applying capsules K1. K2, and K3 to at least a portion of a surface of a first material;

(iv) Activating of capsules K1 and K2 to form an epoxy adhesive;

(v) Activating the at least one capsule K3 simultaneously or sequentially;

(vi) Bonding at least a portion of a surface of a second material to the surface of the first material.

The substance N3 in the capsule K3 comprises an adhesive or a sealing material and is preferably selected from the group consisting of silicones, silicone adhesives and polyurethane adhesives.

In certain embodiments, the quantitative ratio of the epoxy adhesive to the further adhesive (based on amount) can range from about 9:1 to 1:9, preferably in the range of from 5:1 to 1:5, more preferably of from 4:1 to 1:4.

The materials to be bonded can in turn be selected from the group consisting of metal, plastic, wood, paper, textile, fabric, yarn, fiber composite materials, or combinations thereof. Preference is given to aluminum or die-cast aluminum.

In one embodiment of the method according to the invention, the capsules are applied to a material in a layer thickness of not more than about 4000 μm, not more than about 2000 μm, not more than about 1000 μm, not more than about 400 μm, not more than about 300 μm, not more than about 200 μm, not more than about 150 μm.

The selection of the appropriate layer thickness of the application is chosen in such a way that by means of the selected activation mechanism, a sufficient number of the applied capsules are activated. Preferably at least 90% of the capsules are activated, more preferably at least 95% of the capsules, even more preferably at least 98% of the capsules.

As described above, the material of the capsule can also have an influence on the activation. For example, different degrees of crosslinking of (co)polymers can be used to achieve different activation time points, so that the various substances of the system can be released at different time points. A suitable material for the shell is polymethylmethacrylate, which has different degrees of crosslinking with different capsules. Alternatively, the (co)polymers described above, with different hydrophilicity (or hydrophobicity) can be used to control the activation of the capsules through the shell material.

Alternatively, the different time points of activation can also be achieved by the different number of shells for the different capsules described above.

In the method according to the invention, the sequential activation of different capsules can also be achieved by a temperature change. While one of the capsules is activated at temperature T1, at least one of the other capsules is activated at temperature T2, which is different from temperature T1.

The other activation mechanisms such as change in pressure, pH, UV radiation, osmosis, temperature change, light, change in humidity, addition of water, ultrasound, by enzymes, by diffusion, by dissolution of the capsule, degradation control, erosion or the like can also be used in the method according to the invention.

Optionally, the materials to be bonded or their surfaces can be pretreated before bonding, for example to remove an oxide layer from metal surfaces. These pretreatment steps often have to be repeated more frequently in industry because the materials cannot be processed so quickly and the adhesives only have a very short pot life.

As previously described, by applying the system to a surface to be bonded, the method according to the invention allows. In principle, to prevent the re-formation of an oxide layer or to "protect" the surface by the applied capsules and then to continue the further processing at a desired time by activating the capsules.

This means that work steps can be saved or even outsourced. By applying the capsules to the material to be bonded or its surface, an intermediate product can be obtained which, if necessary, can be transported to another location (e.g. another plant) where processing can be continued, e.g. by selective activation of the capsules.

The method according to the invention also makes it possible for the various components of a multi-component adhesive to be applied to the materials or their surfaces in capsules, and for the multi-component adhesive to be activated at a later, desired time. With conventional systems, it is not yet possible for the two components of a multi-component adhesive to be applied (unreactively) to one and the same material or its surface, since the components would then already be reacting. In some cases, therefore, the two different components are applied to the different parts to be bonded, but this requires an additional work step compared with the method according to the invention.

Therefore, the method according to the invention enables the use of multi-component adhesive systems in which the second material is not coated with adhesive. The method according to the invention also makes it possible for the second material not to be subjected to any pretreatment prior to bonding.

In another aspect, the present invention is directed to a material to which a multi-component system according to the invention is applied.

The multi-component system according to the invention can be incorporated in an environmental medium. This environmental medium can, for example, comprise an adhesive, whereby the adhesive of the environmental medium is not located in a capsule. The environmental medium may be pasty.

The material to which the multi-component system and, if applicable, the environmental medium have been applied can be dried after application. In a preferred embodiment, the material is storage-stable, i.e, the applied multi-component system can be used even after storage and can be used according to the invention. In storage tests, the capsules of the invention were stored at room temperature for 6 months. During this time, no leakage of the adhesive or agglutination of the capsules was observed.

In one embodiment, the multi-component system according to the invention is applied to a carrier material, which is preferably a polymer film, a paper or a fabric. The application can be carried out together with an environmental medium, which is preferably an adhesive that is not in a capsule. The application is performed on at least one of the two surfaces of the substrate. One such embodiment may form an adhesive tape that bonds by activating the capsules. The surface to which the multi-component system of the invention has been applied can be protected by a liner which is removed prior to use. In one embodiment, the multi-component system of the invention is applied to both sides of the carrier material to form a double-sided adhesive tape.

In one embodiment, the material is a polymeric film, paper or fabric on which the multi-component system is applied to at least one surface of the material in an environmental medium, preferably in an adhesive that is not in a capsule. It is understood that both sides of the adhesive tape can be protected by a liner which is removed prior to application. The capsule system can be activated by the mechanisms described above.

Another aspect of the present invention is the use of the multi-component system according to the invention for medical purposes, in particular for the (re)association of human or animal tissue.

Therefore, another aspect of the invention is the application of the multi-component system according to the invention in the treatment of wounds and wound healing. In this regard, the system according to the invention can be carried out in the (re)association of human or animal tissue by suturing or bonding. As previously described, pharmaceutically active ingredients can be incorporated into the capsules as well as other materials. The multi-component system according to the invention can either be applied directly to the wound or the suture, or the suture yarn can be coated with the multi-component system according to the invention and activated after the wound has been sutured.

Accordingly, another aspect of the invention also relates to a suture yarn coated with a multi-component system of the invention.

In another aspect, the present invention comprises a method comprising the following method steps:

Providing a multi-component system according to the invention;

Activating at least one of the capsules K1, K2 and/or K3 by at least one of the following mechanisms: change in pressure, pH, UV radiation, osmosis, temperature change, light, change in humidity, addition of water, ultrasound, by enzymes, diffusion, dissolution, degradation control, erosion, or the like; wherein the activation of the capsule(s) can occur at the following time points;

(i) The activation of the at least one capsule K1 occurs at the same time or at a different time point than the activation of the at least one capsule K2;

(i) In the case that the at least one capsule K1 and the at least one capsule K2 are linked to each other, the activation of the at least one capsule K1 and the at least one capsule K2 is preferably performed simultaneously;

(iii) In the case that the at least one capsule K3 is present, the activation or the at least one capsule K3 occurs at a different time point than the activation of the at least one capsule K1.

Figure 2:
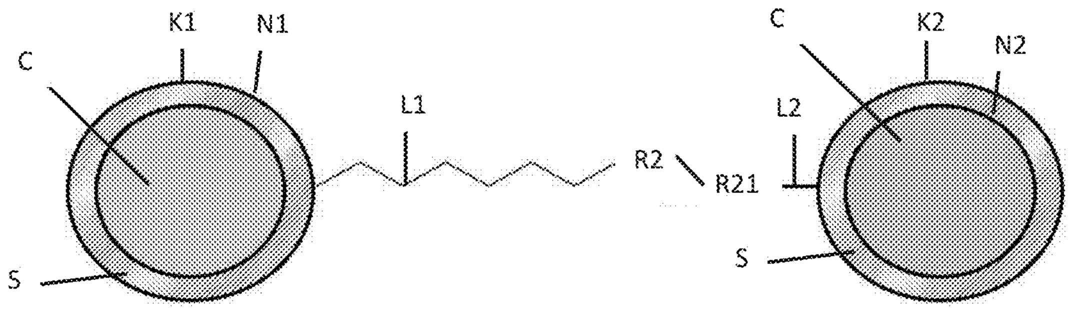
FIG. 2 shows another embodiment of a multi-component system according to the invention with a first substance and a second substance.
Figure 3:
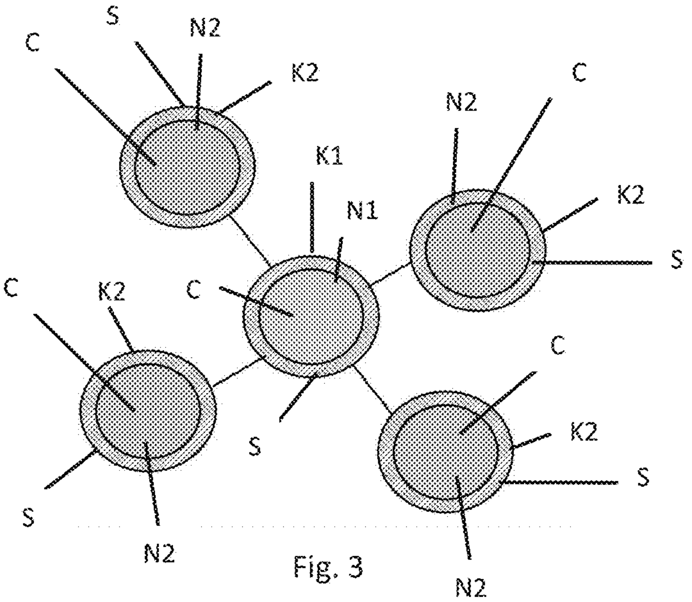
FIG. 3 shows a further embodiment of a multi-component system according to the invention as shown in FIG. 1 or FIG. 2.
Figure 4:
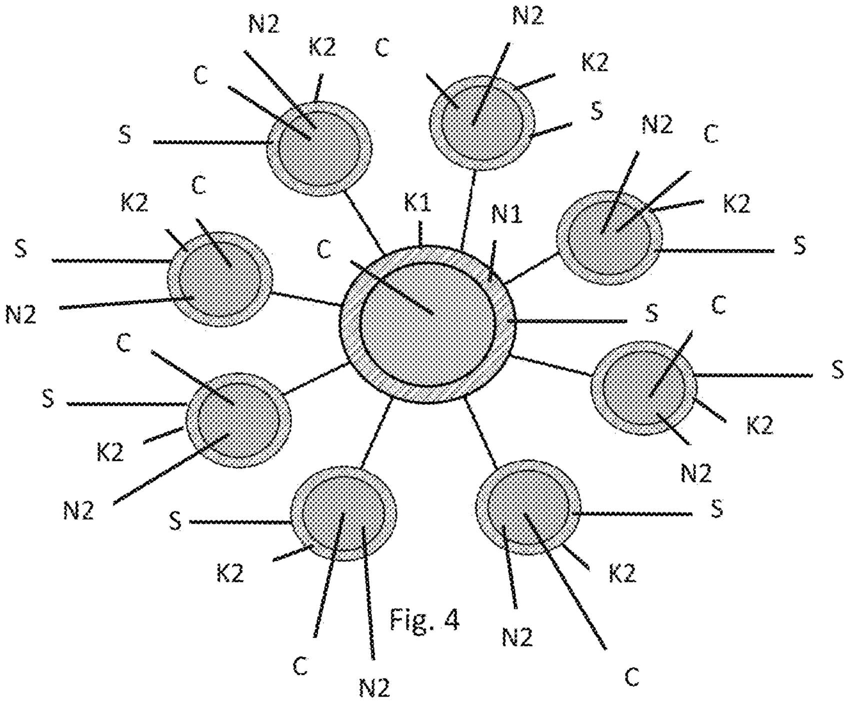
FIG. 4 shows a further embodiment of a multi-component system according to the invention as shown in FIG. 1, FIG. 2 or FIG. 3.
Figure 5:
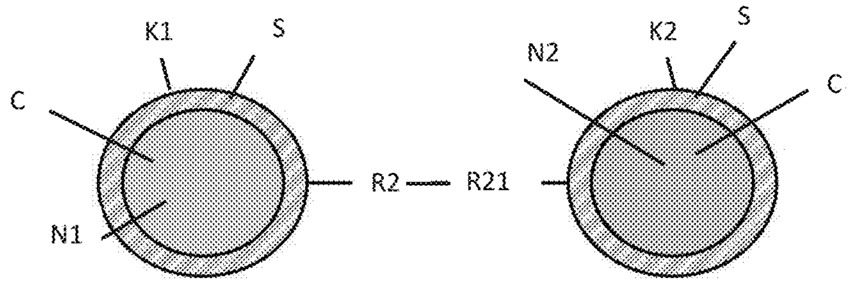
FIG. 5 shows an embodiment of an inter-crosslinking of two different substance portions/capsule population according to the invention.
Figure 6:
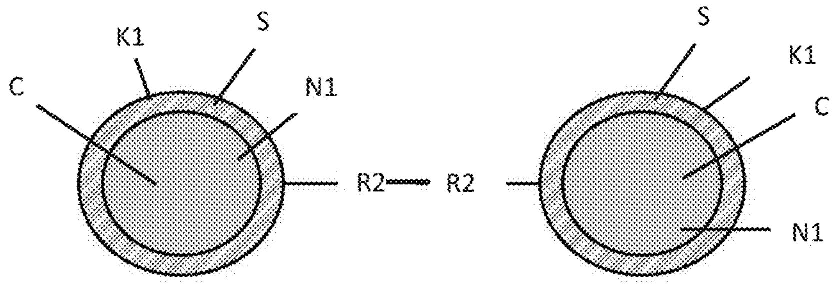
FIG. 6 shows an embodiment of an intra-crosslinking of two equal substance portions/capsule population according to the invention.
Figure 7:
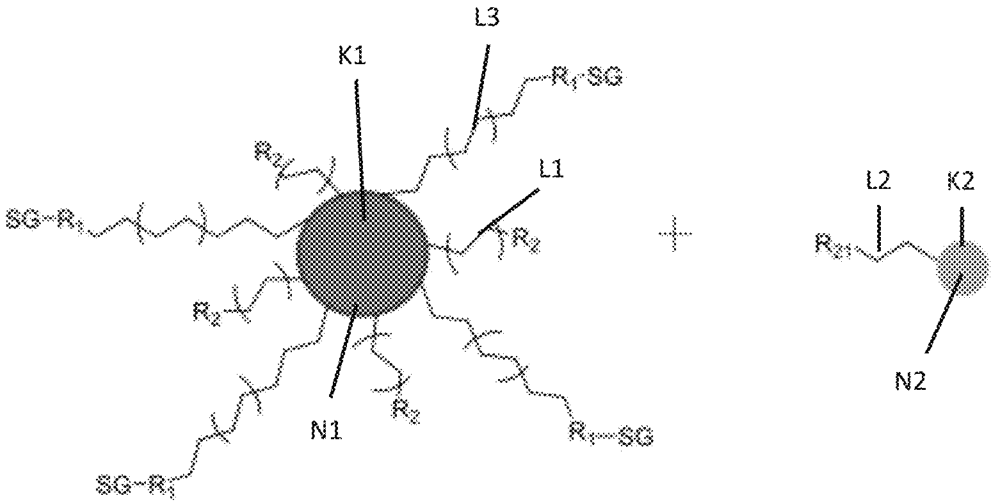
FIG. 7 shows an embodiment of a two-component system according to the invention.
Figure 8:
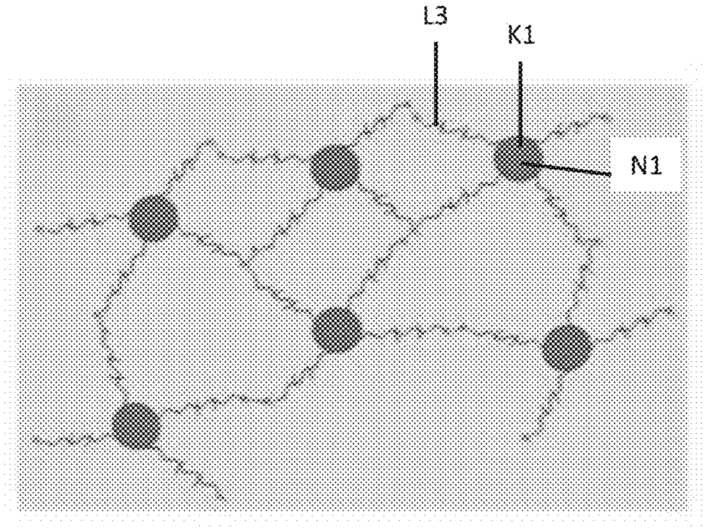
FIG. 8 shows an embodiment of an intra-crosslinked capsule system according to the invention.
Figure 9:
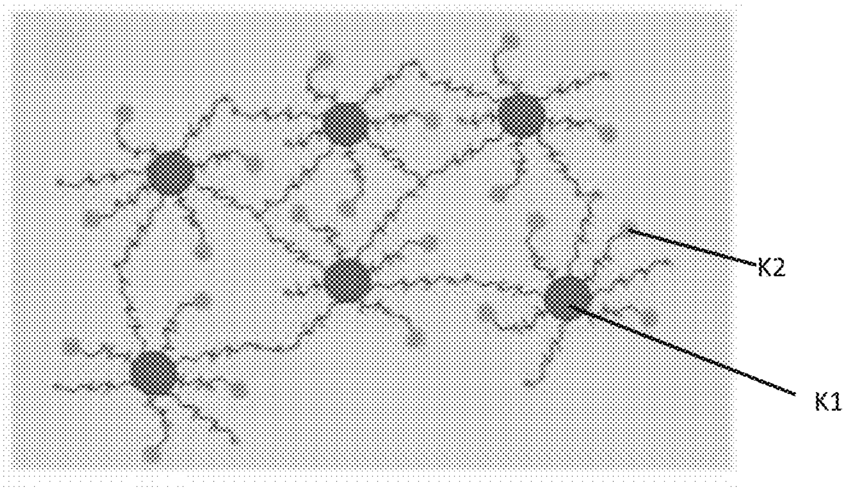
FIG. 9 shows an embodiment of an inter- and intra-crosslinked two-component system according to the invention as shown in FIG. 7.
Figure 10:
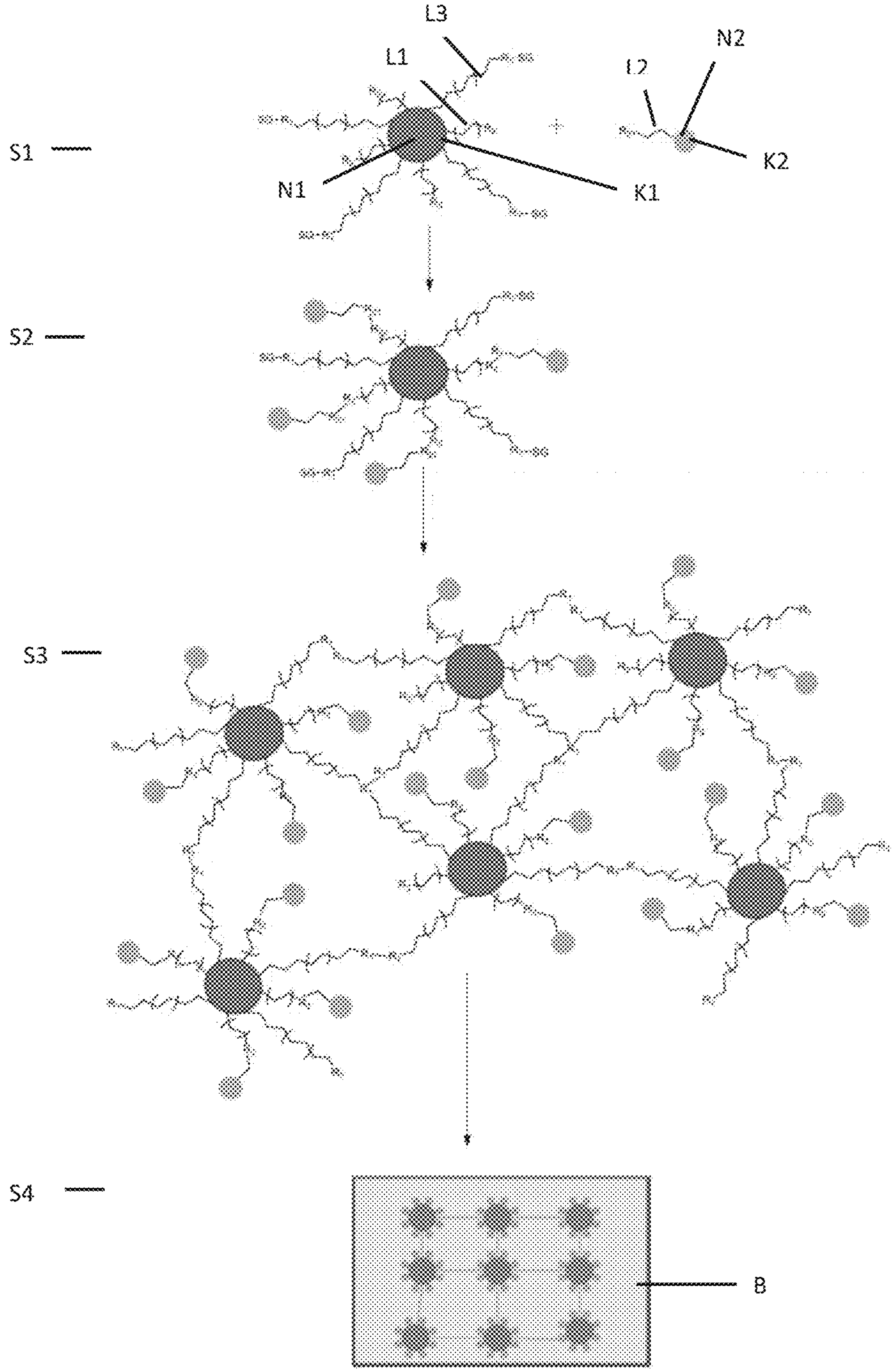
FIG. 10 shows a flowchart of the workflow of preparing a two-component adhesive tape according to the present invention.
Figure 11A:
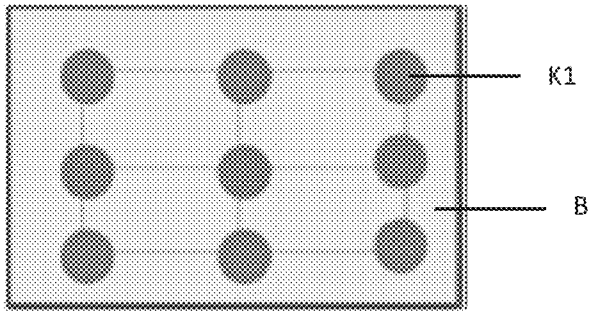
FIG. 11A shows an embodiment of intra-crosslinked capsules of a single component system according to the present invention.
Figure 11B:
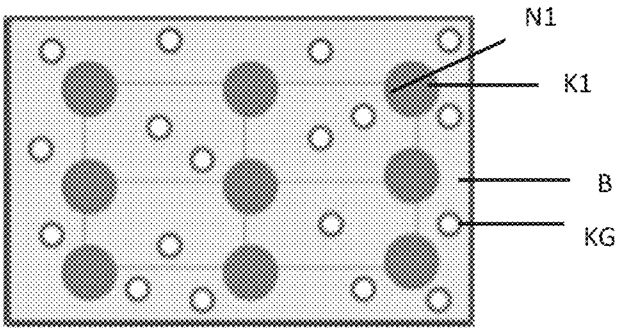
FIG. 11B shows an embodiment of intra-crosslinked capsules of a one-component system and non-crosslinked gas-filled capsules according to the present invention.
Figure 12A:
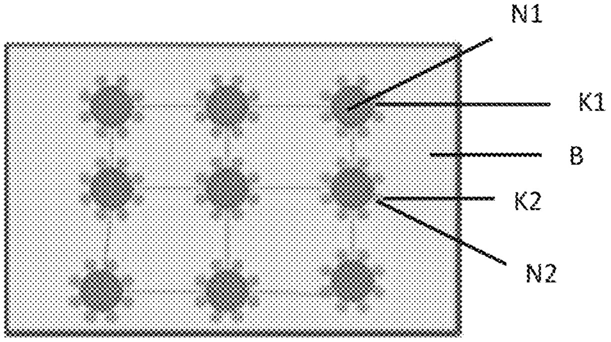
FIG. 12A shows an embodiment of inter- and intra-crosslinked capsules of a two-component system according to the present invention.
Figure 12B:
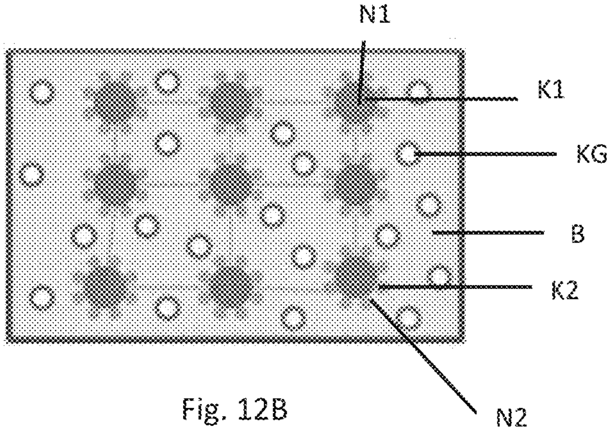
FIG. 12B shows a schematic representation of inter- and intra-crosslinked capsules of a multi-component system and non-crosslinked gas-filled capsules according to the present invention.
Figure 13:
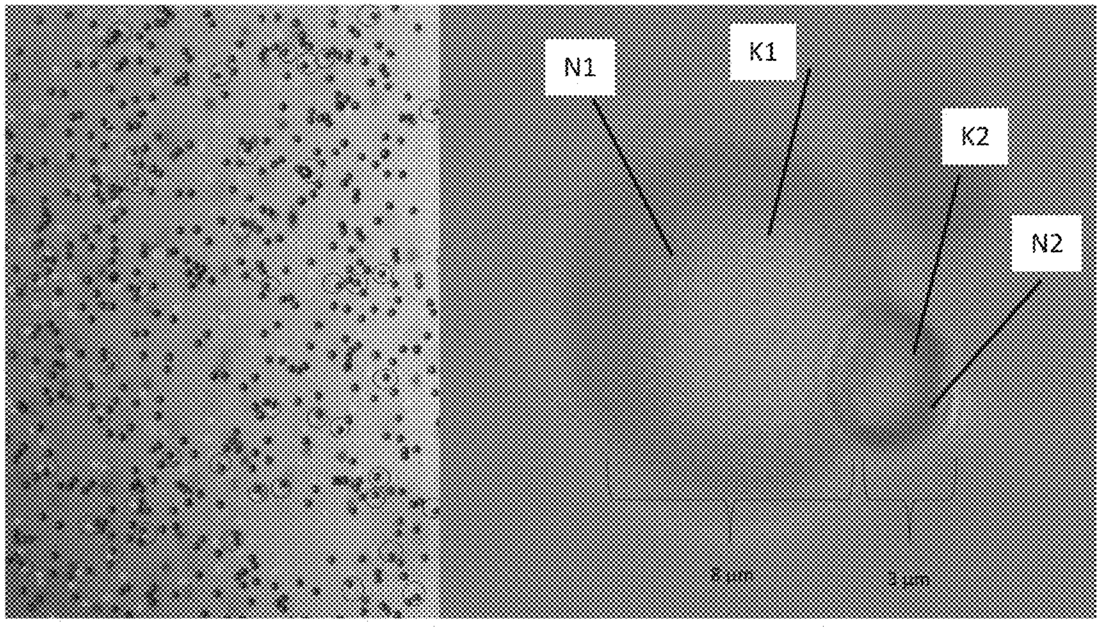
FIG. 13 shows an illustration of the binding ratios of microcapsules in a two-component system according to the present invention.
Figure 14:
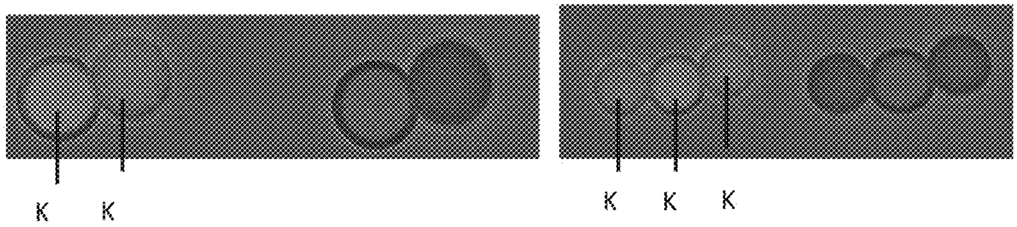
FIG. 14 shows an illustration of the binding according to the invention of microcapsules with the same size but with a different functionalization.
Figure 15:
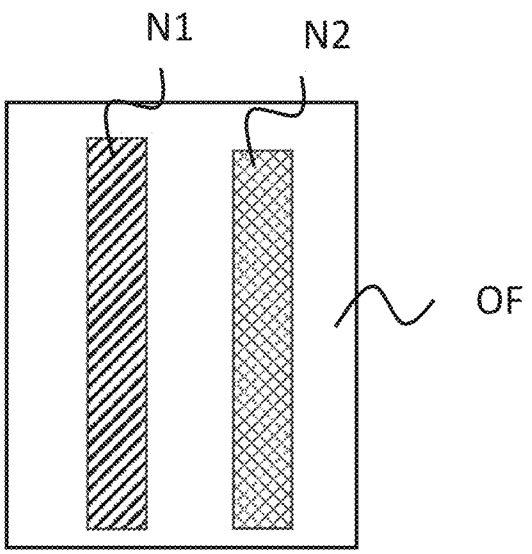
FIG. 15 shows a further embodiment of a multi-component system according to the invention with a first substance N1 and a second substance N2.
Figure 16:
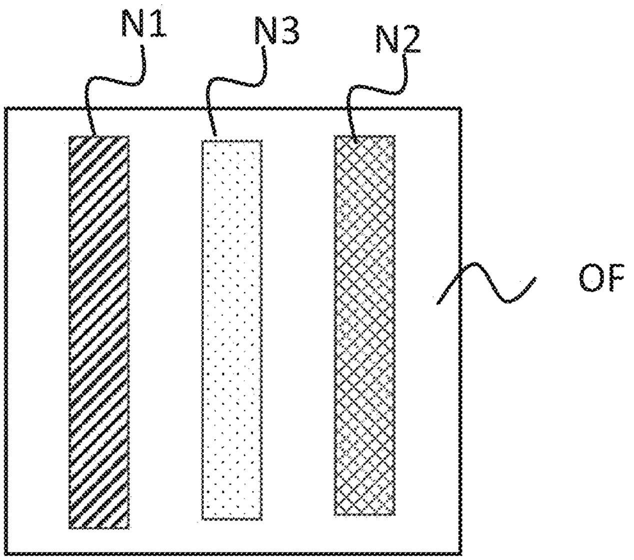
FIG. 16 shows another embodiment of a multi-component system according to the invention with a first substance N1, a second substance N2 and a third substance N3.
Figure 17:
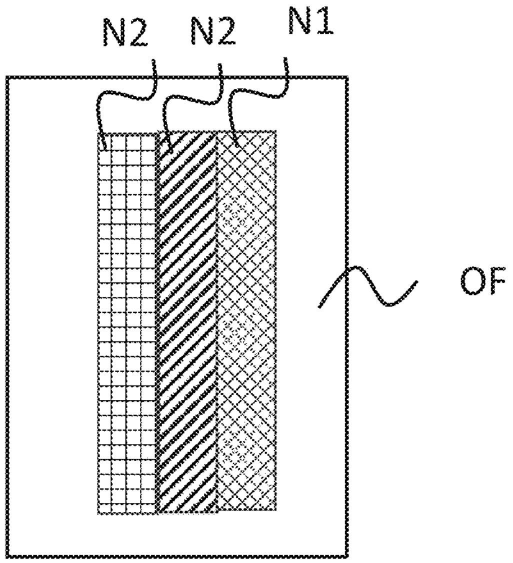
FIG. 17 shows a further embodiment of a multi-component system according to the invention with a first substance N1, a second substance N2 and a third substance N3.
Figure 18:
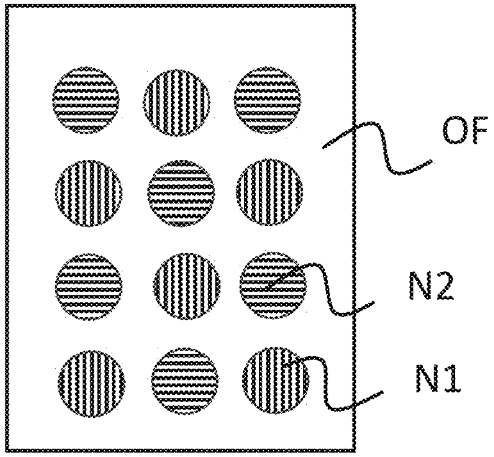
FIG. 18 shows a further embodiment of a multi-component system according to the invention with a first substance N1 and a second substance N2.
Figure 19:
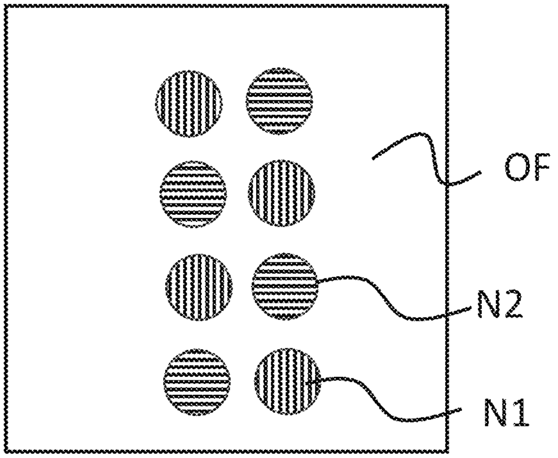
FIG. 19 shows a further embodiment of a multi-component system according to the invention with a first substance N1 and a second substance N2.

It is shown:

FIG. 1 an embodiment of a multi-component system according to the invention with a first substance and a second substance;

FIG. 2 another embodiment of a multi-component system according to the invention with a first substance and a second substance;

FIG. 3 a further embodiment of a multi-component system according to the invention as shown in FIG. 1 or FIG. 2;

FIG. 4 a further embodiment of a multi-component system according to the invention as shown in FIG. 1, FIG. 2 or FIG. 3;

FIG. 5 an embodiment or an inter-crosslinking of two different substance portions/capsule population according to the invention;

FIG. 6 an embodiment of an intra-crosslinking of two equal substance portions/capsule population according to the invention;

FIG. 7 an embodiment of a two-component system according to the invention;

FIG. 8 an embodiment of an intra-crosslinked capsule system according to the invention;

FIG. 9 an embodiment of an inter- and intra-crosslinked two-component system according to the invention as shown in FIG. 7;

FIG. 10 a flowchart of the workflow of preparing a two-component adhesive tape according to the present invention;

FIG. 11A an embodiment of intra-crosslinked capsules of a single component system according to the present invention;

FIG. 11B an embodiment of intra-crosslinked capsules of a one-component system and non-crosslinked gas-filled capsules according to the present invention:

FIG. 12A an embodiment of inter- and intra-crosslinked capsules of a two-component system according to the present invention:

FIG. 12B a schematic representation of inter- and intra-crosslinked capsules of a multi-component system and non-crosslinked gas-filled capsules according to the present invention;

FIG. 13 an illustration of the binding ratios of microcapsules in a two-component system according to the present invention:

FIG. 14 an illustration of the binding according to the invention of microcapsules with the same size but with a different functionalization;

FIG. 15 a further embodiment of a multi-component system according to the invention with a first substance N1 and a second substance N2;

FIG. 16 another embodiment of a multi-component system according to the invention with a first substance N1, a second substance N2 and a third substance N3;

FIG. 17 a further embodiment of a multi-component system according to the invention with a first substance N1, a second substance N2 and a third substance N3;

FIG. 18 a further embodiment of a multi-component system according to the invention with a first substance N1 and a second substance N2;

FIG. 19 a further embodiment of a multi-component system according to the invention with a first substance N1 and a second substance N2

Figure 20:
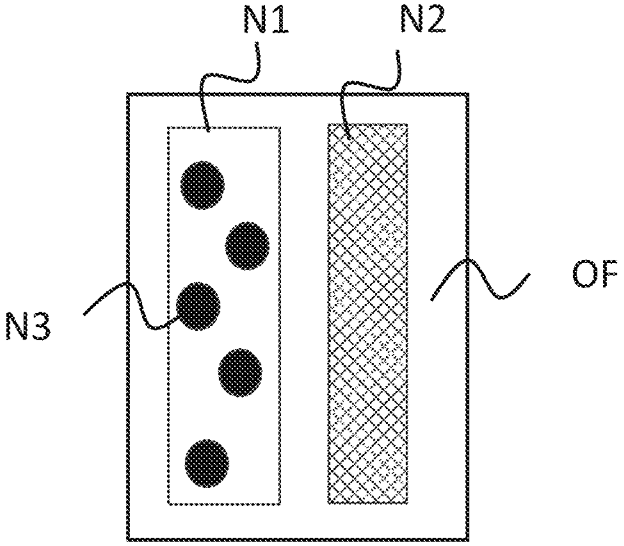
FIG. 20 shows a further embodiment of a multi-component system according to the invention.
Figure 21:
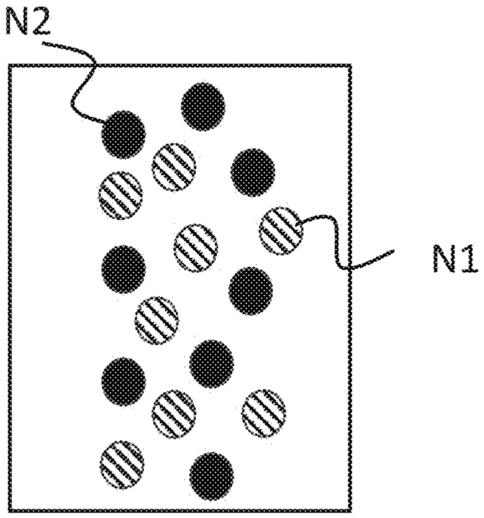
FIG. 21 shows a further embodiment of a multi-component system according to the invention.
Figure 22:
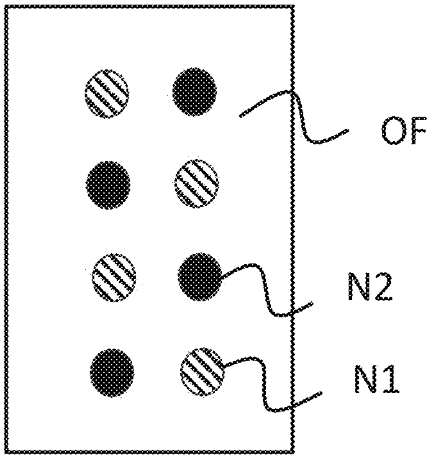
FIG. 22 shows a further embodiment of a multi-component system according to the invention.
Figure 23:
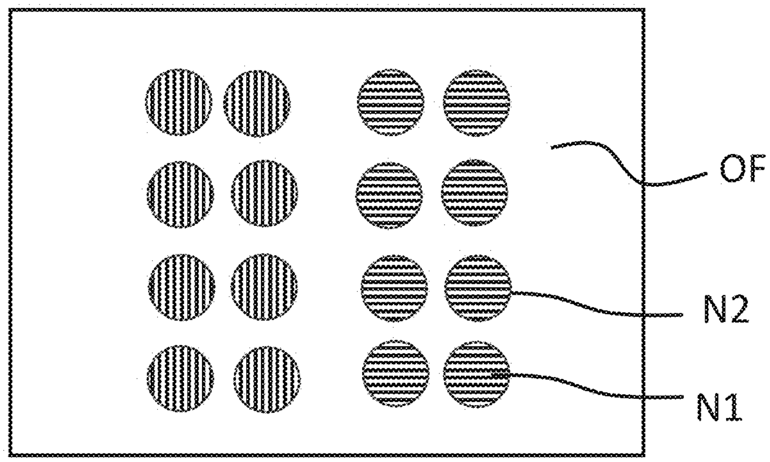
FIG. 23 shows a further embodiment of a multi-component system according to the invention.
Figure 24:
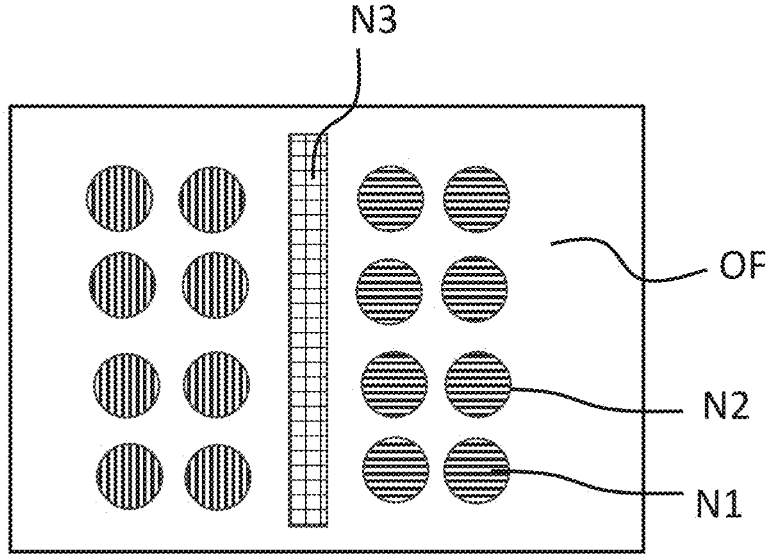
FIG. 24 shows a further embodiment of a multi-component system according to the invention.
Figure 25:
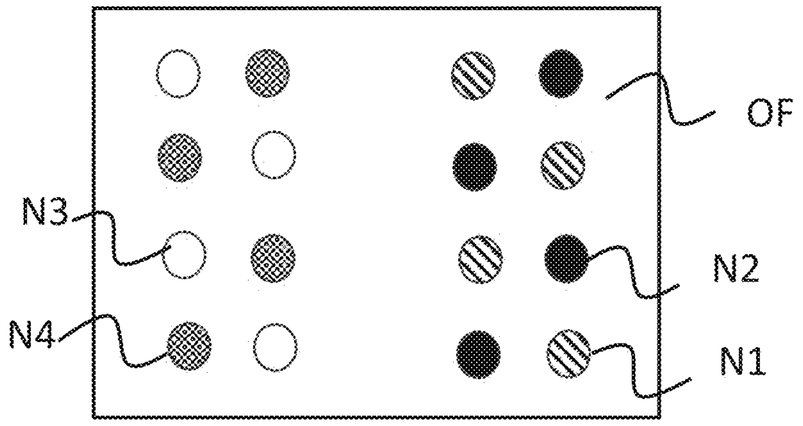
FIG. 25 shows a further embodiment of a multi-component system according to the invention.
Figure 26:
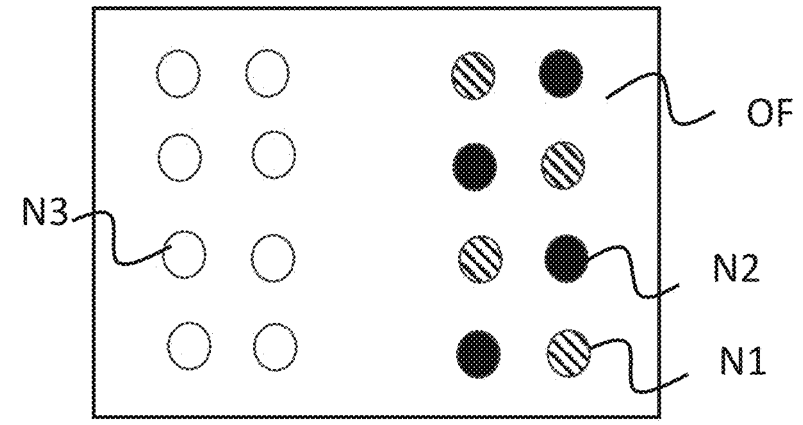
FIG. 26 shows a further embodiment of a multi-component system according to the invention.
Figure 27:
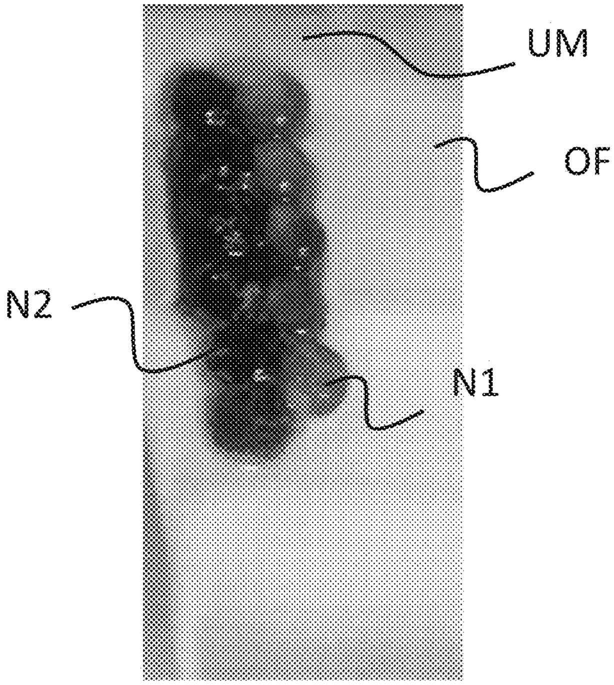
FIG. 27 shows an embodiment of a multi-component system according to the invention incorporated into an environmental matrix.
Figure 28:
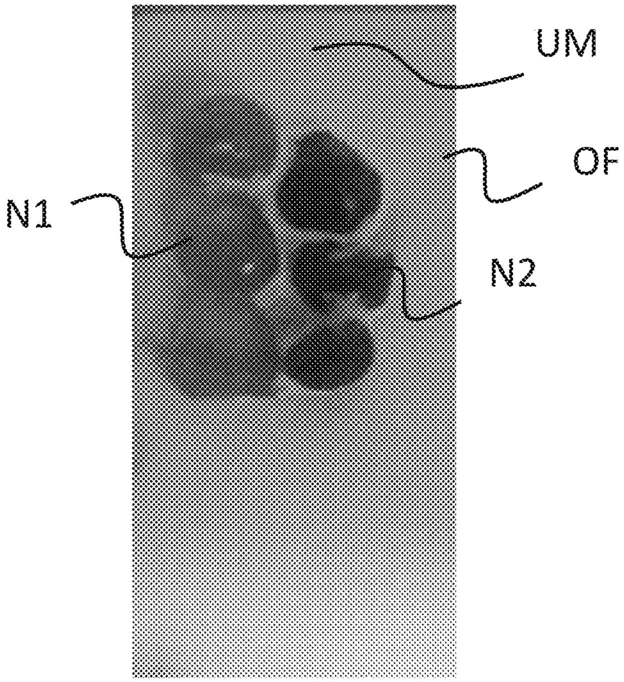
FIG. 28 shows a further embodiment of a multi-component system according to the invention incorporated into an environmental matrix.
Figure 29:
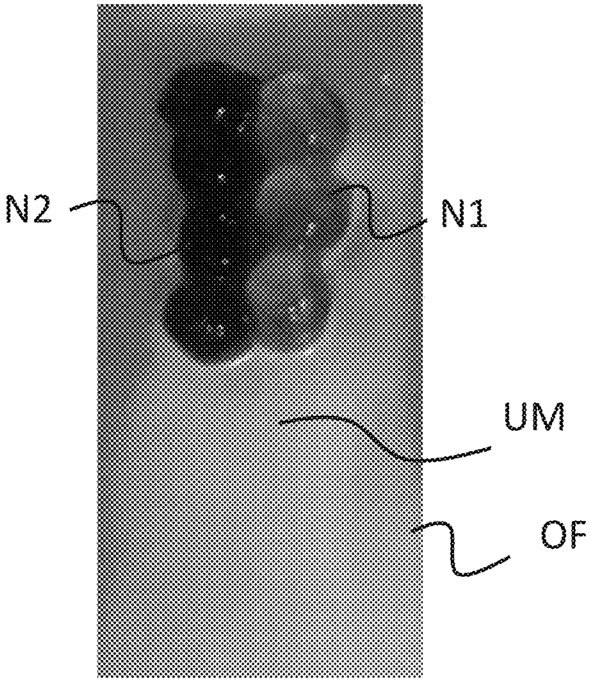
FIG. 29 shows a further embodiment of a multi-component system according to the invention, incorporated into an environmental matrix.
Figure 30:
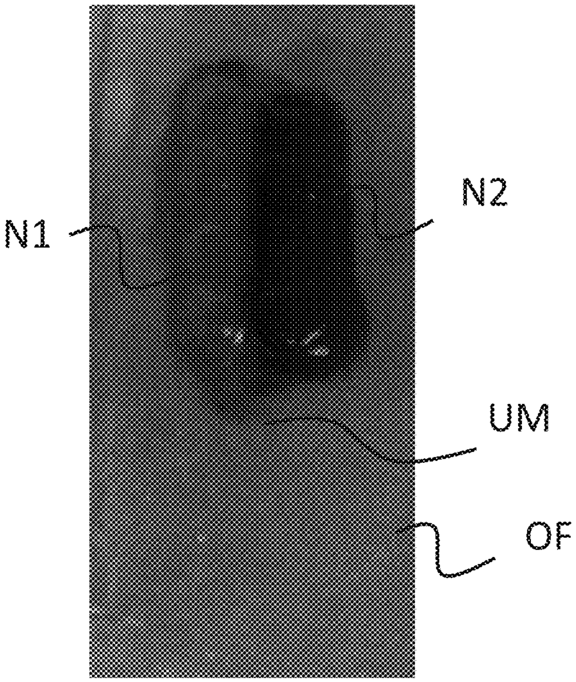
FIG. 30 shows a further embodiment of a multi-component system according to the invention, incorporated into an environmental matrix.
Figure 31:
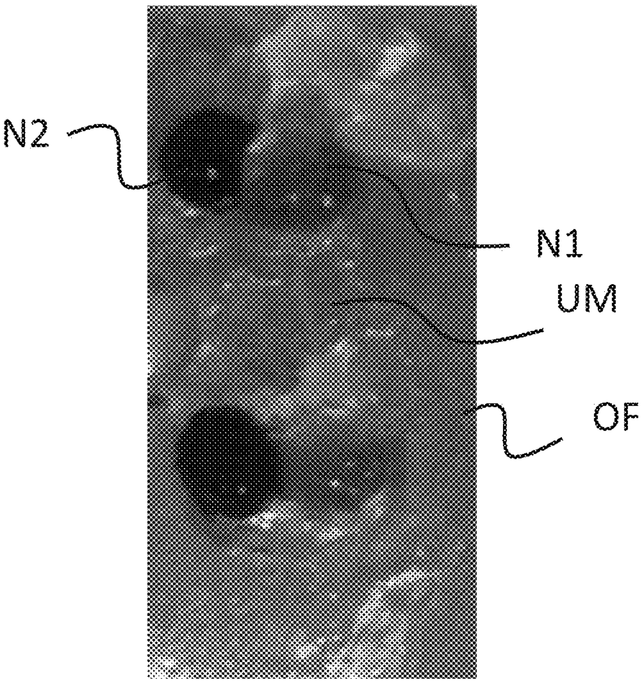
FIG. 31 shows a further embodiment of a multi-component system according to the invention, incorporated into an environmental matrix.
Figure 32:
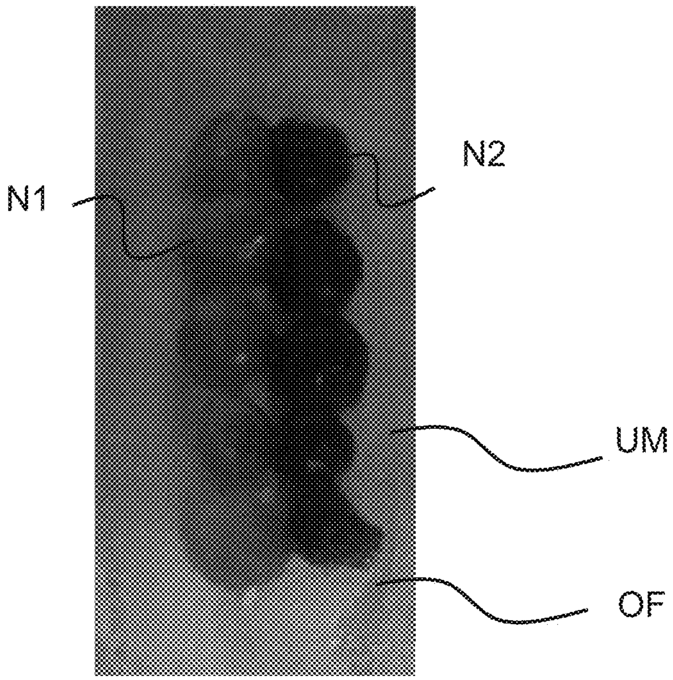
FIG. 32 shows a further embodiment of a multi-component system according to the invention, incorporated into an environmental matrix.
Figure 33:
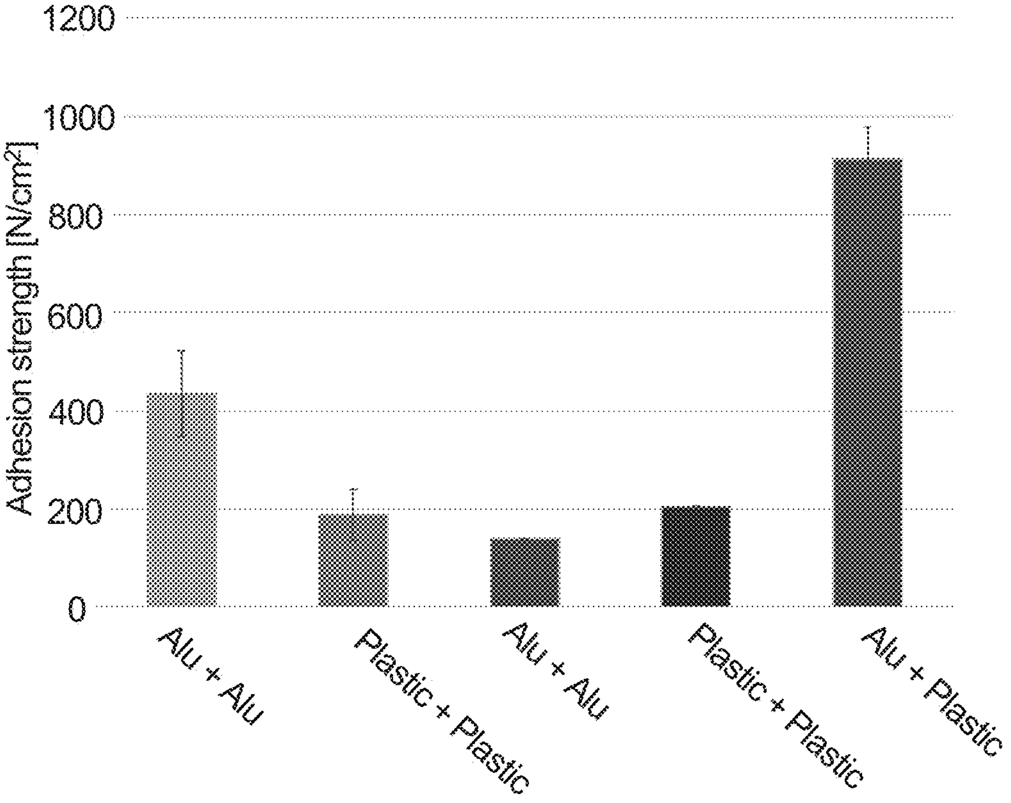
FIG. 33 shows the increased effect of a hybrid adhesive according to the invention compared with the use of individual adhesive components.

FIG. 20 a further embodiment of a multi-component system according to the invention:

FIG. 21 a further embodiment of a multi-component system according to the invention:

FIG. 22 a further embodiment of a multi-component system according to the invention:

FIG. 23 a further embodiment of a multi-component system according to the invention;

FIG. 24 a further embodiment of a multi-component system according to the invention:

FIG. 25 a further embodiment of a multi-component system according to the invention;

FIG. 26 a further embodiment of a multi-component system according to the invention;

FIG. 27 an embodiment of a multi-component system according to the invention incorporated into an environmental matrix;

FIG. 28 a further embodiment of a multi-component system according to the invention incorporated into an environmental matrix;

FIG. 29 a further embodiment of a multi-component system according to the invention, incorporated into an environmental matrix;

FIG. 30 a further embodiment of a multi-component system according to the invention, incorporated into an environmental matrix;

FIG. 31 a further embodiment of a multi-component system according to the invention, incorporated into an environmental matrix;

FIG. 32 a further embodiment of a multi-component system according to the invention, incorporated into an environmental matrix; and FIG. 33 the increased effect of a hybrid adhesive according to the invention compared with the use of individual adhesive components.

Figure 34A:
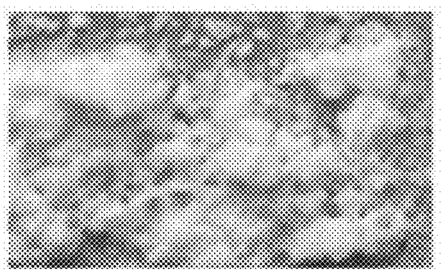
FIG. 34A shows a two-component system according to the invention without linkage of the capsules before activation.
Figure 34B:
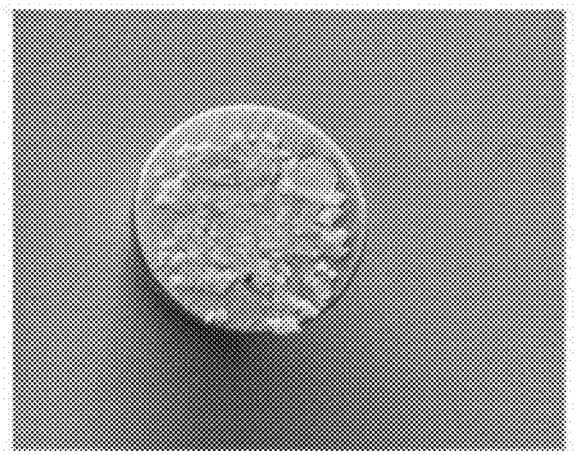
FIG. 34B shows a two-component system according to the invention without linkage of the capsules after activation.
Figure 34C:
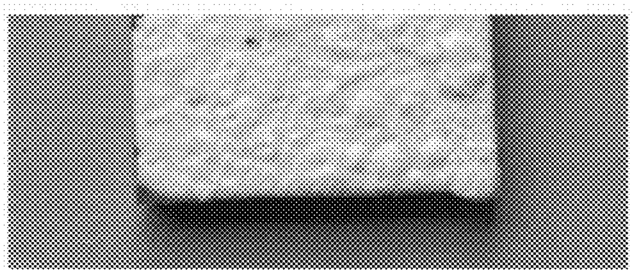
FIG. 34C shows a two-component system according to the invention with linkage of the capsules before activation.
Figure 34D:
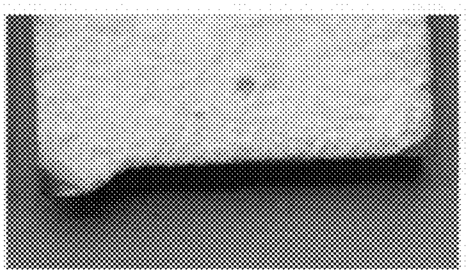
FIG. 34D shows a two-component system according to the invention with linkage of the capsules after activation.

FIGS. 34A-34D Multi-component system according to the invention, which was applied in the environmental medium using the ASTM D823 standard method with a layer thickness of 200 μm. FIGS. 34A and 34B show a two-component system according to the invention without linkage of the capsules before activation (FIG. 34A) and after activation (FIG. 34B), respectively. FIGS. 34C and 34D show a two-component system according to the invention with linkage of the capsules before activation (FIG. 34C) and after activation (FIG. 34D), respectively.

Figure 35:
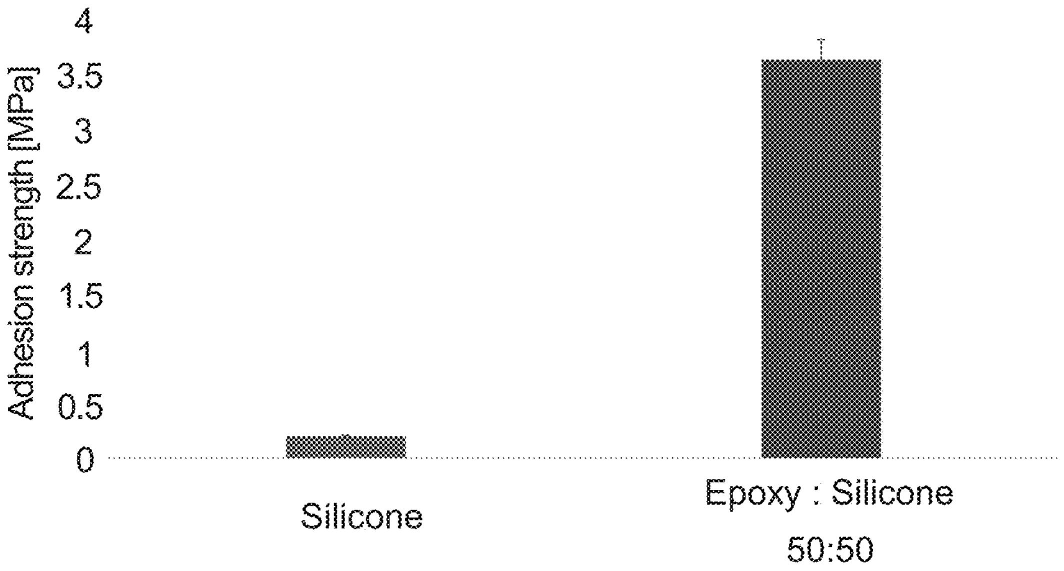
FIG. 35 shows a comparison of the adhesive strength of a multi-component system according to the invention with a commercially available silicone adhesive (Elastosil® E43).

FIG. 35 Comparison of the adhesive strength of a multi-component system according to the invention with a commercially available silicone adhesive (Elastosil® E43).

FIG. 38 Comparison of the adhesive strength of a multi-component system according to the invention with different mixing ratios of silicone and epoxy adhesive FIG. 1 shows an embodiment of a multi-component system according to the invention with a first substance N1 and a second substance N2.

In this embodiment, the multi-component system can be activated.

It is possible that the first substance N1 and the second substance N2 are present in multiple substance portions.

In this embodiment, the first substance N1 is present in a capsule population K1.

In other words, in this embodiment, the first substance portions are first capsules K1.

In this embodiment, the second substance N2 is present in a capsule population K2.

In other words, in this embodiment, the second substance portions are second capsules K2.

Generally, it is possible that a substance portion of the first substance N1 and/or the second substance N2 is arranged in a capsule K, in particular a nanocapsule and/or microcapsule.

The substance portion forms a core C (also called core) in K1 and K2 respectively, which is surrounded by a capsule shell S (also called shell). This is therefore a "core-shell" construct. In principle, however, core-shell-shell constructs are also conceivable.

In this embodiment, the first substance portions are formed with at least a first functional group R2 and provided with a first linker L1.

In this embodiment, the second substance portions are formed with at least one second functional group R21 and provided with a second linker L2.

In this embodiment, the first functional group R2 reacts with the second functional group R21 via a predefined interaction and links them to one another.

In this embodiment, the distance of the functional groups to the respective substance portion is determined by the respective linker L.

The capsules shown in FIGS. 2-4 are identical in structure to the capsules K1 and K2 shown in FIG. 1.

In this embodiment, the first substance portions are formed with at least a first functional group R2 and provided with a first linker L1.

In this embodiment, the second substance portions are formed with at least one second functional group R21 and provided with a second linker L2.

In this embodiment, the first functional group R2 reacts with the second functional group R21 via a predefined interaction and links them to one another.

In this embodiment, the distance of the functional groups to the respective substance portion is determined by the respective linker L.

It is possible that the first linker L1 is longer than the second linker L2, cf. FIG. 2.

Alternatively, it is possible that the second linker L2 is longer than the first linker L1.

Alternatively, it is possible that both linkers L1 and L2 have the same length.

FIG. 3 shows an embodiment of a multi-component system according to the invention as shown in FIG. 1 or FIG. 2.

In this embodiment, the first substance portions and the second substance portions are different.

In other words, in this embodiment, the capsules K1 of the first capsule population are different from the capsules K2 of the second capsule population.

In this embodiment, the first substance portions are linked or linkable to a greater number of substance portions than the second substance portions.

In other words, in this embodiment, the capsules K1 are linked or linkable to a larger number of capsules K than the capsules K2.

Alternatively, it is possible that the second substance portions are linked or linkable to a larger number of substance portions than the first substance portions.

In other words, it is possible that the capsules K2 are linked or linkable to a larger number of capsules K than the capsules K1.

FIG. 4 shows a further embodiment of a multi-component system according to the invention as shown in FIG. 1, FIG. 2, or FIG. 3.

In this embodiment, the first substance portions and the second substance portions have substantially different sizes.

In this embodiment, the first capsules K1 have a substantially larger size than the second capsules K2.

In general, a capsule K1 of a first substance N1 can have a different size than a capsule K2 of a second substance N2, in particular wherein the capsule K1 of the first substance N1 is larger than the capsule K2 of the second substance N2.

Alternatively, it is possible for the second substance portions to have a substantially larger size than the first substance portions.

Alternatively, it is possible for the first substance portions and the second substance portions to be substantially identical in size.

Not shown is that the first substance portions can have a substantially identical size and/or that the second substance portions can have a substantially identical size.

FIG. 5 shows an embodiment of an inter-crosslinking of two different substance portions according to the invention.

In this embodiment, one capsule K1 and one capsule K2 are inter-crosslinked.

In this embodiment, a capsule K1 and a capsule K2 are inter-crosslinked via functional groups R2 and R21.

FIG. 6 shows an embodiment of an intra-crosslinking of two identical substance portions according to the invention.

In this embodiment, two capsules K1 are intra-crosslinked.

In this embodiment, the two capsules K1 are intra-crosslinked via the functional groups R2-R2.

FIG. 7 an embodiment of a two-component system according to the invention.

In this embodiment, the two-component system is a two-component microcapsule system.

In this embodiment, the two-component system is a two-component microcapsule system that has not yet reacted with each other via a predefined interaction.

In particular, two different capsule populations K1 and K2 are shown, where a first substance N1 is in the first capsule K1 and a second substance N2 is in the second capsule K2.

The capsules K1 and K2 shown are exemplary for a plurality of capsules K1 and K2. e.g. to be called capsule populations.

In this embodiment, the first substance N1 in the capsule K1 is a first adhesive component.

In this embodiment, the second substance N2 in the second capsule K2 is a second adhesive component.

In other words, the first substance and the second substance are components of a multi-component adhesive, in particular a two-component adhesive.

It is generally possible that the two different capsule populations K1 and K2 were prepared in separate batch reactors.

The capsules K1 and K2 of the two capsule populations are functionalized.

The first capsules K1 were formed with two different linkers L1 and L3 of different lengths and with different functional groups R1 and R2 on the surface (surface functionalization).

In other words, the functional groups R are formed heterogeneously.

In an alternative embodiment, it is possible that the functional groups R are formed homogeneously.

The second capsules K2 were formed with the linker L2 and with the functional group R21.

The functional group R21 of the second capsule K2 reacts covalently with the functional group R2 of the first capsule K1.

In this embodiment, it is possible that the first capsules K1 are linked or linkable to a larger number of capsules K than the second capsules K2.

In an alternative embodiment, it is possible that the second capsules K2 are linked or linkable to a larger number of capsules K than the first capsules K1.

The linker L3 and the functional group R1 should crosslink the first capsules K1 (intra-crosslinking).

Via the linker L1 and the functional group R2 and the linker L2 and the functional group R21, the capsules K2 are covalently linked to the first capsule K1 (inter-crosslinking).

By activating both capsules K1 and K2, the contents of the capsules K1 and K2 can be released, resulting in a mixing of both components.

It is generally possible to determine the number of second capsules K2 that bind to the first capsules K1 by the density of surface functionalization or number of functional groups R2 of the first capsule K1.

Generally, two reactive substances can be encapsulated separately from each other in the capsules K1 and K2 and linked in a certain ratio via, among others, covalently (e.g. click chemistry), via weak interaction, biochemically (e.g. blotin-streptavidln), or other means.

It is generally possible that more than two different capsules Kn encapsulate more than two different substances, e.g. reactive substances.

It is generally possible that the different capsules Kn are formed with more than two linkers Ln and with different functional groups Rn.

It is generally possible for a linker L to be any form of link between a capsule and a functional group.

It is generally possible that with heterogeneous functionalization, a functional group R can be used to bind to surfaces, fibers or textiles.

As with existing capsule systems, any conceivable substance can be introduced into the capsules K1 and/or K2 and/or Kn.

Activation of the two-component system can be accomplished by at least one change in pressure. pH, UV radiation, osmosis, temperature, light intensity, humidity, induction, or the like.

In general, a two-component capsule system could be implemented in any medium.

FIG. 8 shows an embodiment of an intra-crosslinked capsule system according to the invention.

In this embodiment, the intra-crosslinked capsule system according to the invention is an intra-crosslinked microcapsule system.

A single component system is shown.

A capsule population K1 is shown.

The capsules K1 are filled with a substance N1.

In this embodiment, the capsules K1 are filled with an adhesive.

In this embodiment, the capsules K1 are filled with a one-component adhesive.

Alternatively, the capsules K1 can be filled with any gaseous, solid, viscous and/or liquid substance.

Alternatively, the capsules K1 can be filled with living organisms and/or viruses.

The capsules K1 were functionalized.

The capsules K1 were provided with inkers L3.

Not shown is that the capsules K1 are formed with functional groups R1 (at inker L3).

The linkers L3 crosslink the capsules K1 with each other (intra-crosslinking).

The distance between the capsules K1 can be determined by the length of the linker L3.

Depending on the density of the surface functionalization R1, the degree of intra-crosslinking of the capsules K1 can be determined.

The length of the linker L3 should be chosen so that the radius of the contents of the discharged liquid of the capsules K1 slightly overlaps with the contents of the adjacent capsules K1 to ensure crosslinking.

For a higher viscosity environmental medium (such as an adhesive tape), the length of the linker L3 would be smaller than for a lower viscosity medium such as a paste or liquid.

FIG. 9 shows an example of an inter- and intra-crosslinked two-component system according to the invention as shown in FIG. 7.

The first capsules K1 and the second capsules K2 are filled with different substances.

In this embodiment, the capsules K1 have a substantially identical size.

In this embodiment, the capsules K2 have a substantially identical size.

In this embodiment, the capsules K1 and the capsules K2 have different sizes.

In an alternative embodiment, it is possible that the capsules K1 and the capsules K2 have a substantially identical size.

The basic system corresponds to the illustration in FIG. 8.

Moreover, the first capsules K1 are formed heterogeneously with a linker L1.

A second capsule population K2 binds to the linker L1, cf. FIG. 1.

In other words, the two-component system has a (network) structure with interspaces, the (network) structure being formed by the first capsules K1, and at least one capsule K2 being, at least in sections, arranged in each of the interspaces.

It is generally possible for the two-component capsules K1 and K2 with different contents, to be introduced into the gas phase. For example, they could be used in inhalers or other drug delivery systems. The inactivated capsules reach the site of action where they are activated and the contents are released. Surfaces could also be coated with this dispersion.

It is generally possible for the two-component capsules K1 and K2 with different contents to be introduced into a pasty medium. For example, a two-component adhesive could be used for this purpose. The paste is inert and can be processed well until the capsules are activated and react with each other. The ideal mixing ratio of the adhesives is determined by the ratio of the first and second capsules K1 and K2 as described above.

Also in liquid systems, the advantage of the ideal composition of the two-component capsule systems can be used. Since both capsules K1 and K2 of the two-component capsule system are in close proximity, it is very likely that the capsules K1 and K2 react faster and more defined with each other than individually in dispersion.

FIG. 10 shows a flow chart of the workflow for preparing a two-component adhesive tape according to the invention.

FIG. 10 is essentially based on a two-component capsule system as shown in FIG. 7.

Overall, the preparation of a two-component adhesive tape according to the invention is divided into four steps S1-S4.

In a first step S1, the first capsules K1 and the second capsules K2 are functionalized, cf. FIG. 7.

In the present two-component system, the first capsules K1 are formed heterogeneously with two linkers L1 and L3 with functional groups R1 and R2.

In a separate batch, the second population of capsules K2 is functionalized with the linker L2 with the functional group R21.

The functional group R21 is to be selected so that it reacts (covalently) with the functional group R2 of the first capsule K1 in the later reaction step.

In a second step S2, the functionalized second capsules K2 are added to the functionalized first capsules K1.

The functional groups R2 and R21 bind (covalently) to one another (inter-crosslinking).

It is generally possible for a third or any number of additional capsule populations K3-Kn to also be added to a first capsule population K1 and/or a second capsule population K2.

Each additional capsule population K3-Kn can in turn be functionalized with at least one functional group.

In a third step S3, the heterogeneous capsule dispersion from the previous step S2 is introduced into the still low-viscosity pressure-sensitive adhesive, in this case an adhesive tape (B).

A predetermined (intra)-crosslinking reaction occurs, which is formed through the entire area of the adhesive tape (B).

In a fourth step S4, the crosslinked two-component capsule populations are applied and the adhesive tape B is dried.

The viscosity of the adhesive tape B increases significantly, but the network remains homogeneously distributed on the adhesive tape.

It is shown that in step S1. In order to prevent the first capsules K1 from prematurely crosslinking with each other during functionalization, a protection group SG can still be formed on the functional group R1 of the linker L3.

It is further shown that in step S3 the protection groups SG are removed.

Removal of the protection group can allow intra-crosslinking of the capsules K1.

Application possibilities in different environmental media:

Based on the workflow described here for the preparation of a two-component adhesive tape according to the invention, the two-component capsule system can alternatively be applied in other media and with all encapsulated substances.

Conceivable environmental media include gas, liquid, pasty, low- and high-viscosity media, and solid surface coatings.

It is generally possible for the capsules K to be nanocapsules or microcapsules.

Generally, the method enables the preparation of further multi-component systems comprising at least one first substance and at least one second substance, wherein the first substance and the second substance are present in multiple substance portions, wherein the multi-component system can be activated, comprising the following steps:

- the first substance portions are formed with at least one first functional group R2 and provided with a first linker L1,
- the second substance portions are formed with at least one second functional group R21 and provided with a second linker L2,
- the first functional group R2 reacts with the second functional group R21 via a predefined interaction so that they are linked to one another, and
- the distance of the functional groups R to the respective substance portion is determined by the respective linker L.

It is generally possible that the first substance portions are formed with at least one third functional group R1 and provided with a third linker L3.

It is generally possible that the each of the third functional groups R1 has at least one protection group SG, so that only correspondingly functionalized substance portions of the first substance can bind to the substance portions of the first substance.

It is generally possible that the method further comprises at least the step that the protection groups SG are initially present and are removed only when the first substance portions are to be linked to one another by means of the third functional groups R1.

It is generally possible that the functional groups R1 each have at least one protection group, so that only correspondingly functionalized substance portions of the second substance can be linked to the substance portions of the first substance.

Further, it is generally possible for the method of preparing a mufti-component system to further comprise at least the step of initially having the protection groups and removing them only when the first and second substance portions are to be linked to one another by means of the first and second functional groups R2, R21.

FIG. 11A shows a schematic representation of intra-crosslinked capsules of a one-component system in a high-viscosity system according to the present invention.

In this embodiment, the crosslinked one-component system is incorporated into a high-viscosity system as described in FIG. 8.

The high viscosity system is an adhesive tape B.

Alternatively, other high-viscosity, liquid, gaseous, paste or low-viscosity systems are conceivable.

In this embodiment, the adhesive tape B is a one-sided adhesive tape B.

Alternatively, double-sided variants of adhesive tape B are also possible.

Usually there is a diffusion problem in high-viscosity systems, so that the content of the capsules K1 in the adhesive tape B does not enable the crosslinking between the two materials to be bonded.

The (intra)-crosslinking of the one-component system allows the spacing and degree of crosslinking of the capsules K1 to be selected so that the contents of the capsules K1 form a crosslinking system through the high-viscosity adhesive.

This basic principle can also be extended to a two-component system as shown in FIG. 12A. There, the (inter- and intra-) crosslinking mechanism is used.

It is not shown that the two-component system can also be introduced into the adhesive tape only with prior inter-crosslinking of capsules K1 and capsules K2.

FIG. 11B shows a schematic representation of intra-crosslinked capsules of a one-component system and non-crosslinked, gas-filled capsules according to the present invention.

Alternatively, the non-crosslinked capsules can also be filled with solid or liquid substances.

In addition to the intra-crosslinked capsules K1 of the one-component system according to FIG. 11A, a further population of non-crosslinked, gas-filled capsules KG can be introduced into the high-viscosity adhesive, such as an adhesive tape B, which release the gas when they burst and thus either create free space for the liquid component of the capsules K1 or enable the adhesive tape to be removed again.

It would also be conceivable to incorporate a dissolving placeholder (e.g., fibers or the like) in the adhesive tape B.

This would create channels in which the liquid adhesive of the capsules K1 can spread and crosslink over a large area within the adhesive tape B.

Another possibility would be to fill the liquid-filed capsules K1 into tubes and to place them in the adhesive tape B.

Thus, cross-linking could occur to the extent of the tube length.

This basic principle can also be extended to a two-component system as shown in FIG. 12B.

Here, the inter- and intra-crosslinking mechanism is used.

In addition to the first capsules K1 of the single-component system, a second capsule population K2 is introduced.

This mechanism enables introducing a two-component adhesive system into an adhesive tape B.

The described systems are not limited to single-component capsule systems or two-component capsule systems.

Depending on the size and functionalization of the respective system in question, any number of capsule populations Kn can be linked and crosslinked to one another.

By combining the individual components, a very wide range of new functionalities and thus new possible applications can be developed.

In the following, the preparation of polymethylmethacrylate microcapsules is described as an example:

First, 2.5 g of polymethylmethacrylate (PMMA) is dissolved in 11.5 mL of toluene. Then, oil is mixed in. For microencapsulation, the homogeneous solution is added to 45 mL of a 1 wt.-% polyvinyl alcohol (PVA) solution. The emulsion is stirred at 800 rpm for 30 min. The toluene is then evaporated. The resulting microcapsules K with a PMMA coating material are washed with distilled water and centrifuged at 5,000 rpm and dried overnight at 50° C. in a vacuum oven.

Then, the surface of the microcapsules is silanized. The microcapsules are placed in a fluidized bed reactor. A 5% aqueous (3-aminopropyl)triethoxysilane (APTES) solution is used as the coating material. After the coating process, the microcapsules are dried for 1 h at 80° C. in a vacuum oven to obtain optimal binding of the aminosilane to the surface. In addition, the surface of microcapsules K can be activated with oxygen plasma before the reaction.

For the inter-crosslinking of two capsule populations K1 and K2 (capsules K with different contents), the complementary capsule population K can be functionalized with carboxyl groups. Here, the procedure is analogous to the silanization described above. However, instead of (3-aminopropy)triethoxysilane (APTES), a sliane-PEG-COOH is used.

Subsequently, the capsules K can be sieved with a sieve of different pore sizes to increase the monodispersity. This has the advantage that in the subsequent linking process, the volume ratios of the two capsule contents can be precisely determined via the size of the capsules K.

Then the microcapsule linking takes place. The first microcapsule K1 is functionalized with primary amines, while the second microcapsule K2 is functionalized with carboxyl groups. In the next step, 80 μL of a 10% carboxyl functionalized microcapsule suspension is added to an aqueous solution and 7 μL of a 2 M (1-ethyl-3-(3-dimethylaminopropyl)carbodiimide) solution (EDC solution) and 7 μL of a 0.3 M N-hydroxysuccinimide solution (NHS solution) are added and stirred for one hour at room temperature. The carboxyl function is converted to an activated ester. Then, in the same ratio as the carboxyl microcapsules K2, the amine microcapsules K1 are added to the solution and linked together for two hours at room temperature with gentle stirring. Subsequently, the functional groups that did not react with each other are blocked with ethanolamine and the capsules are filtered off through a sieve, washed with distilled water and dried in a vacuum oven at 50° C. for one hour.

In FIG. 13, it can be seen that most of the microcapsules K are linked to one another in a 1:1 ratio.

In addition, there are a few microcapsules K that are linked in a 1:2 ratio or are not linked to one another at all.

To ensure the quality of the two-component microcapsules K, the microcapsules K are then purified via a sieve with different pore sizes according to the size or their binding ratio. The binding ratio of the microcapsules K can also be influenced via the number of functional groups on the microcapsules K.

It is possible that microcapsules K with the same size (e.g. 8 μm) but with different functionalization were linked to one another. In the case of functionalization with linear polymers, the 1:1 linkage predominates, cf. FIG. 14. In the case of functionalization with polymers that exhibit multivalence, the triple linkage predominates.

It is also possible that the functionalization of microcapsules occurs via adsorption.

Especially in the case of microcapsules with plastic surfaces, the functionalization of microcapsules can be achieved via adsorption. Preferred examples of plastic surfaces are acrylic resin, polylactic acid, nylon 6 and 12, epoxy resins, and polystyrene.

For adsorption to the surface of the microcapsules, alkyl chains or primary amines are preferably used.

The second functional group can be freely selected and is thus available for microcapsule linking in the next step.

The plastic surface of the microcapsules can be formed directly in the microencapsulation process or in a second step by a multilayer microcapsule obtained in this way.

In an alternative embodiment, the second microcapsule population can be prepared from and/or coated with metal particles or a metal shell.

The two microcapsule populations with 4-aminobenzenthiol as binder of both microcapsule populations are added.

The primary amine binds to the microcapsules with the plastic surface via adsorption, and the thiol group binds to the metal surface.

Furthermore, functionalization is possible during the microencapsulation process as described in WO2017192407.

Accordingly, for example, a mixture comprising water (20 mL), ethyl acetate (5 mL), sodium bicarbonate (0.580 g), about 1.0 mg Sudan Black and a drop of Tween 20 is mixed vigorously (5 minutes at 500 rpm) at room temperature using a mechanical stirrer (about 500 mL). To the mixture, 77 mg of 1,3-bischlorosulfonylbenzene is added, followed by stirring for about 3 minutes. The mixture is then treated with 3,5-diaminobenzoic acid and stirred vigorously for another 72 hours. To observe the reaction taking place in the mixture, aliquots are taken thirty minutes after vigorous stirring begins, and at 12 hour intervals thereafter. On microscopic observation, the aliquots show the formation capsules with a diameter of 1 to 2 micrometers, with the dye Sudan black contained therein. The reaction is completed after several hours. It is postulated that the capsules have several —COOH groups on the surface.

Furthermore, functionalization during the microencapsulation process is possible according to the further methods described in WO2017192407.

Accordingly, a second substance portion can be prepared in a separate batch approach using the same method, but with primary amines on the surface.

Subsequently, the microcapsule population can be activated with COOH on the surface as in the example before with EDC/NHS, the amine capsule population is added and the capsules bind covalently to each other. In the next step, the capsules can be washed (filtered if necessary) and dried. The capsules obtained in this way can then be incorporated into a further environmental medium.

For example, another conceivable method of preparing is described in Yip, J and Luk, MYA, Antimicrobial Textiles, Woodhead Publishing Series in Textiles, 2016, Pages 19-48, 3-Microencapsultion technologies for antimicrobial textiles.

It is conceivable that the microcapsules with metal particles can also be applied via charge.

Intra-crosslinking is possible.

It is conceivable that after the preparation of the microcapsules with metal particles on the surface, a mixture of alcohol and mercaptans (SAM polymer) is added to the capsules.

For functionalized thiols, the second functional group can be chosen arbitrarily. The thiol bonds bind to the metal surface. The remainder, i.e. the second functional group of the thiol molecule, is available as a functional group for the microcapsule linkage.

By selecting one or more SAM polymers to be added to the microcapsules, the surface functional groups can be formed homogeneously or heterogeneously.

In addition, the length of the linker can be determined by a suitable mercaptan.

In one embodiment, it is possible to select ethanethiol as a short linker. For a longer linker, an 11-mercaptoundecannoic can be selected.

Furthermore, it is possible to bind the thus functionalized surface of the microcapsules with a second polymer, e.g. with a PEG, in order to further increase the length of the linker.

Disulfites, phosphoric acids, silanes, thiols, and polyelectrolytes can be used as SAM surfaces. In particular, acetylcysteine, dimercaptosuccinic acid, dimercaptopropanesulfonic acid, ethanethiol (ethyl mercaptan), dithiothreltol (DTT), dithioerythritol (DTE), captopril, coenzyme, A, cysteine, peniciflamine, 1-propanethiol, 2-propanethiol, glutathione, homocysteine, mesna, methanethiol (methyl mercaptan), and/or thiophenol can be used.

Inter-crosslinking is possible.

The microcapsules with the metal nanoparticles can be prepared as described above.

A mixture of alcohol and dithioether can then be added.

One of the functional groups R is protected.

In this way, the microcapsules are functionalized.

The number of metal nanoparticles on the surface of the microcapsules can then be used to determine the number or density of functionalization and thus the number of functional groups.

This enables determining the number of microcapsules K2 that react with one another via intra- or inter-crosslinking.

In the next step, the microcapsules can be inserted into the desired environmental medium, such as a pressure-sensitive adhesive (or the like).

For inter-crosslinking, the use of 4-isocyanate butane-1-thiol is conceivable, wherein the NCO groups are protected.

Here, the removal of the protection groups and thus the activation of the functional groups R takes place in the pressure-sensitive adhesive, which is still low in viscosity. The NCO groups thus de-protected can crosslink with one another in an aqueous environment (e.g. the solvent of the pressure-sensitive adhesive) to form urea.

FIG. 15 shows a further embodiment of a multi-component system according to the invention with a first substance N1 and a second substance N2.

A multi-component system comprising a first substance N1 and a second substance N2 is shown, wherein the first substance N1 and the second substance N2 are each present in one respective portion.

Alternatively, multiple substance portions of the first substance N1 and multiple substance portions of the second substance N2 can be present.

Alternatively, the multi-component system can comprise at least one third substance N3, which can be present in one or more substance portions.

In this embodiment, the first substance N1 and the second substance N2 are attached to a surface OF.

In this embodiment example, the first substance N1 and the second substance N2 are applied to a surface OF as tracks.

The two substance portions are initially placed separately on the surface OF, i.e. without any contact points or contact lines with each other.

Alternatively, the substance portions can also be attached to the surface OF with contact points and/or contact lines, cf. FIG. 17.

Alternatively and/or additionally, the first substance N1 and/or the second substance N2 can be applied as dots, spheres, lines, circles, ellipses or in other geometric or non-geometric shapes, cf. FIG. 18 and FIG. 19.

Generally, the first substance N1 and/or the second substance N2 can be applied to a subsection of the surface OF (e.g., at the edge, in one corner, in multiple corners, along a path or circle, etc.) or to the entire surface OF.

Generally, the at least one substance portion of the first substance N1 and/or the second substance N2 can be applied to the surface OF in a geometric pattern or in an irregular manner.

In this embodiment, the surface OF is a metal surface.

Alternatively, the surface can be a plastic surface, film, wood surface, textile surface, paper surface, wax surface, or the like.

In this embodiment, the first substance N1 and the second substance N2 were applied with a dispenser.

In this embodiment, the first substance N1 is a one-component adhesive.

In this embodiment, the second substance N2 is a one-component adhesive.

Alternatively, the first substance N1 and/or the second substance N2 can be no adhesive, but a sealing, insulating, thermally conductive, electrically conductive, antibiotic, antimicrobial or other component.

The first substance N1 and the second substance N2 differ in their properties.

In one embodiment of FIG. 15, the first substance N1 can alternatively be a first component of a two-component adhesive and the second substance N2 can be a second component of a two-component adhesive.

In one embodiment of FIG. 15, the first substance N1 can comprise a first multi-component adhesive having a first composition, and the second substance N2 can comprise a second multi-component adhesive having a second composition.

In one embodiment of FIG. 15, the first substance N1 can comprise an epoxy adhesive having a first composition and the second substance N2 can comprise an epoxy adhesive having a second composition.

In one embodiment of FIG. 15, the first substance N1 can alternatively comprise a multi-component adhesive and the second substance N2 can comprise a one-component adhesive.

In one embodiment of FIG. 15, the first substance N1 can alternatively comprise a first component of an epoxy adhesive, wherein the first component is present in multiple substance portions which are encapsulated, in particular in nanocapsules and/or microcapsules, and the second substance N2 can comprise a second component of an epoxy adhesive, wherein the second component is present in multiple substance portions which are encapsulated, in particular in nanocapsules and/or microcapsules, in particular in nanocapsules and/or microcapsules, and the second substance N2 may comprise a second component of an epoxy adhesive, the second substance N2 being present in a plurality of substance portions the substance portions being encapsulated, in particular in nanocapsules and/or microcapsules.

In one embodiment of FIG. 15, the first substance N1 can alternatively comprise an epoxy adhesive having a first composition and the second substance N2 can comprise a silicone-based adhesive having a second composition.

In one embodiment of FIG. 15, the first substance N1 can alternatively comprise an epoxy adhesive having a first composition and the second substance N2 can comprise a polyurethane adhesive having a second composition.

In one embodiment of FIG. 15, the first substance N1 can alternatively comprise an epoxy adhesive having a first composition and the second substance N2 can comprise an acrylic adhesive having a second composition. In other words, the multi-component system can be a hybrid adhesive system.

In one embodiment of FIG. 15, at least one portion of the first substance N1 and/or the second substance N2 can be arranged in a capsule K, in particular a nanocapsule and/or microcapsule, see FIG. 21 and FIG. 22.

FIG. 16 shows a further embodiment of a multi-component system according to the invention with a first substance N1, a second substance N2 and a third substance N3.

A multi-component system with a first substance N1, a second substance N2 and a third substance N3 is shown, wherein the first substance N1, the second substance N2, and the third substance N3 each are present in a substance portion or adhesive track.

Alternatively, there can be multiple substance portions of the first substance N1, multiple substance portions of the second substance N2, and/or multiple substance portions of the third substance N3.

Alternatively, the multi-component system can comprise at least a fourth substance, which can be present in one or more substance portions.

In this embodiment, the first substance N1, the second substance N2, and the third substance N3 are provided on a surface OF.

In this embodiment, the substances N1, N2, N3 are applied to a surface OF as tracks, with the third substance N3 being present between the first substance N1 and the second substance N2.

The three substance portions are initially arranged on the surface OF separately without any contact points with each other.

Alternatively, the three substance portions can be at least partially in contact with each other; cf. FIG. 17

Alternatively and/or additionally, the first substance N1 and/or the second substance N2 and/or the third substance N3 can be applied as dots, spheres, lines, circles, ellipses or in other geometric or non-geometric shapes.

In this embodiment, the surface OF is a metal surface.

Alternatively, the surface can be a plastic surface, film, wood surface, textile surface, paper surface, wax surface, or the like.

In this embodiment, the first substance N1 is a first component of a two-component adhesive.

In this embodiment, the second substance N2 is a second component of a two-component adhesive.

In this embodiment, the third substance N3 is an inert substance that prevents the reaction between the first substance N1 and the second substance N2 until activation.

FIG. 17 shows a further embodiment of a multi-component system according to the invention with a first substance N1, a second substance N2 and a third substance N3.

A multi-component system comprising a first substance N1, a second substance N2 and a third substance N3 is shown, wherein the first substance N1, the second substance N2 and the third substance N3 are each present in a substance portion.

Alternatively, multiple substance portions of the first substance N1 and/or multiple substance portions of the second substance N2 and/or multiple substance portions of the third substance N3 can be present.

Alternatively, the multi-component system can comprise at least a fourth substance, which can be present in one or more substance portions.

In this embodiment, the first substance N1, the second substance N2, and the third substance N3 are provided on a surface OF.

In this embodiment, the first substance N1, the second substance N2 and the third substance N3 are applied to a surface OF as tracks.

The substance portions are arranged on the surface OF with contact lines (between the first substance N1 and the second substance N2, as well as the second substance N2 and the third substance N3).

Alternatively, Individual contact points would be possible.

Alternatively, contact points and/or contact lines would be possible between only the first substance N1 and the second substance N2 or the second substance N2 and the third substance N3.

Alternatively, the substance portions can also, in particular initially, be arranged on the surface separately, i.e. without contact points or contact lines with each other OF; cf. FIG. 15 or FIG. 16.

Alternatively and/or additionally, the first substance N1 and/or the second substance N2 and/or the third substance N3 can be applied as dots, spheres, lines, circles, ellipses or in other geometric or non-geometric shapes; cf. FIG. 18.

FIG. 18 shows a further embodiment of a multi-component system according to the invention with a first substance N1 and a second substance N2.

A multi-component system with a first substance N1 and a second substance N2 is shown, wherein the first substance N1 and the second substance N2 are present in multiple portions.

Alternatively, only one portion or the first substance N1 and/or one portion of the second substance N2 can be present; cf. FIG. 15.

Alternatively, the multi-component system can comprise at least one third substance, which can be present in one or more substance portions.

In this embodiment, the substance portions of the first substance N1 and the substance portions or the second substance N2 are provided on a surface OF.

In this embodiment, the first substance N1 and the second substance N2 are applied on a surface OF as dots.

The substance portions are initially placed on the surface OF separately, i.e. without contact points or contact lines with each other.

Alternatively, the substance portions can also be arranged on the surface OF with contact points and/or contact lines; cf. FIG. 17.

Alternatively and/or additionally, the first substance N1 and/or the second substance N2 can be applied as spheres, lines, circles, ellipses, paths, lines or in other geometric or non-geometric shapes; cf. FIG. 15.

In this embodiment, the substance portions of the first substance N1 and the substance portions or the second substance N2 are distributed over the entire surface OF.

Alternatively, the substance portions of the first substance N2 and/or the substance portions of the second substance N2 can be distributed only on a subsection of the surface OF, for example in tracks (cf. FIG. 19) or circles, along the edge, in corners, etc.

FIG. 19 shows a further embodiment of a multi-component system according to the invention with a first substance N1 and a second substance N2.

The figure description of FIG. 19 is essentially the same as the figure description of FIG. 18. However, the substance portions of the first substance N2 and the substance portions of the second substance N2 are distributed only in a subsection of the surface OF, in this case in a (double-)track.

Alternatively, the substance portions of the first substance N1 and the substance portions of the second substance N2 can be distributed in multiple tracks on the surface.

Alternatively, the substance portions of the first substance N1 and the substance portions of the second substance N2 can be in separate tracks; cf. FIG. 23.

In general, it is possible that an inert substance (e.g. also in the form of a track) is arranged between individual tracks; cf. FIG. 23.

FIG. 20 shows a further embodiment of a multi-component system according to the invention.

In this embodiment, a first substance N1 and a second N2 are applied to a surface OF as tracks.

In this embodiment, a third substance N3 in multiple substance portions is applied on the first substance N1, here in the form of capsules (in particular microcapsules or nanocapsules).

Alternatively, the third substance N3 can be arranged in the first substance N1 or adjacent to the first substance N1.

In one embodiment of FIG. 20, the first substance N1 can comprise a first component of an epoxy adhesive and the third substance N3 can comprise a second component of an epoxy adhesive, wherein the third substance N3 is present in multiple substance portions, wherein the substance portions are encapsulated, in particular in nanocapsules and/or microcapsules.

In other words, the third substance N3 comprises a component or an epoxy adhesive which is present in capsules, in particular microcapsules or nanocapsules, and the first substance N1 comprises another component of an epoxy adhesive which is not present in capsules but is provided on a surface OF.

Here, the multi-component system also comprises a second substance N2, for example another adhesive (e.g. a silicone adhesive or polyurethane adhesive).

In this embodiment, the capsules can be activated.

In one embodiment of FIG. 20, the first substance N1 and the third substance N3 can represent a two-component adhesive system that can be activated.

In one embodiment of FIG. 20, both components of a two-component adhesive can alternatively be present in capsules.

In one embodiment of FIG. 20, a fourth substance N4, which is encapsulated (for example in the form of microcapsules or nanocapsules), can be linked in, on or to the second substance N2. For example, a component of a polyurethane adhesive can be encapsulated as substance N4, and at least one component of a polyurethane adhesive can be present as substance N3.

In one embodiment of FIG. 20, the second substance N2 can alternatively be present in encapsulated form.

FIG. 21 shows a further embodiment of a multi-component system according to the invention.

A multi-component system with at least one first substance N1 and at least one second substance N2 is shown, wherein the first substance N1 and the second substance N2 are present in multiple substance portions.

In this embodiment, a substance portion of the first substance N1 and the second substance N2 is arranged in a capsule K, in particular a nanocapsule and/or microcapsule.

In this embodiment, the substance portions of the first substance N1 and the substance portions of the second substance N2 are provided on a surface OF.

In this embodiment, the surface OF is a metal surface.

Alternatively, the surface OF can be a wood surface, plastic surface, paper surface, textile surface, film or the like.

In this embodiment, the substance portions of the first substance N1 and the substance portions of the second substance N2 are not arranged at a defined distance from each other.

Alternatively and/or additionally, the substance portions of the first substance N1 and the substance portions of the second substance N2 can be arranged at a defined distance from each other; cf. FIG. 22.

In one embodiment of FIG. 21, the first substance N1 can be a first component of a two-component adhesive, e.g. an epoxy adhesive.

Alternatively, the first substance can be a silicone adhesive or a one-component adhesive.

In one embodiment of FIG. 21, the second substance N2 can be a second component of a two-component adhesive, e.g. an epoxy adhesive.

Alternatively, the second substance can be a silicone adhesive, plastic adhesive or polyurethane adhesive.

In one embodiment of FIG. 21, a substance portion of the first substance N1 and a substance portion of the second substance N2 can alternatively be present in a common capsule K or in a double capsule or multi-component capsule.

In a dual capsule or multi-component capsule, the linkage of one capsule with the first substance N1 and one capsule with the second substance N2 can be achieved by weak interaction and/or covalent bonding.

In one embodiment of FIG. 21, in addition to the capsules of the first substance N1 and the capsules of the second substance N2, capsules with a third substance can be present.

The third substance N3 can also be non-encapsulated.

The third substance N3 can have a further property such as a sealing, heat conducting, insulating, electrically conducting function, etc. The third substance N3 can also have an adhesive property.

The third substance N3 can be, for example, a silicone adhesive and/or polyurethane adhesive.

In one embodiment of FIG. 21, more than three substances can be possible.

In this embodiment, the capsules containing substances N1 and N2 are applied as a pre-applicable adhesive to the surface OF to be bonded.

In one embodiment of FIG. 21, the capsules can be activated by pressure, temperature difference. Induction and/or ultrasound, so that the first substance N1 and/or the second substance N2 is discharged from the capsules.

In general, the activation mechanism and/or the necessary activation energy can be different or the same for the capsules with the first substance N1 and the capsules with the second substance N2.

In this embodiment, the pre-applicable adhesive prevents the formation of an oxide layer on the metal surface OF.

In one embodiment of FIG. 21, the capsules can also be embedded in an environmental matrix, cf. FIGS. 27-32. The environmental matrix allows easy application of the capsules and additionally protects the metal surface OF from oxidation.

The environmental matrix can be, for example, an acrylic paint, or an acrylic varnish, or a water-based adhesive.

For example, the different application patterns of the environmental matrix are analogous to the application patterns in FIGS. 15-20 and 22-25.

FIG. 22 shows a further embodiment of a multi-component system according to the invention.

A multi-component system comprising at least one first substance N1 and at least one second substance N2 is shown, wherein the first substance N1 and the second substance N2 are present in multiple substance portions.

In this embodiment, a substance portion of the first substance N1 and the second substance N2 are each arranged in a capsule K, in particular a nanocapsule and/or microcapsule.

In this embodiment, the substance portions of the first substance N1 and the substance portions of the second substance N2 are provided on a surface OF.

In this embodiment, the substance portions of the first substance N1 and the substance portions of the second substance N2 are arranged at a defined distance from each other.

In particular, both the distance between the individual substance portions of a substance (N1 or N2) and the distance between the substance portions of the different substances are defined.

Alternatively, only the distance between the individual substance portions of a substance (N1 or N2) can be defined or the distance between the substance portions of the different substances.

Alternatively and/or additionally, the substance portions of the first substance N1 and/or the substance portions of the second substance N2 can be arranged at a non-defined distance from each other; cf. FIG. 21.

In one embodiment of FIG. 22, the first substance N1 can be a first component of a two-component adhesive.

Alternatively, the first substance can be a silicone adhesive or a one-component adhesive.

In one embodiment of FIG. 22, the second substance N2 can be a second component of a two-component adhesive.

Alternatively, the second substance can be a silicone adhesive, plastic adhesive, or polyurethane adhesive.

In one embodiment of FIG. 22, in addition to the capsules of the first substance N1 and the capsules of the second substance N2, capsules with at least one further substance can be present (three or more substances in total.

FIG. 23 shows a further embodiment of a multi-component system according to the invention.

The figure description of FIG. 23 is essentially the same as the figure description of FIG. 18. However, the substance portions of the first substance N2 and the substance portions of the second substance N2 are distributed only in subsections of the surface OF, here in tracks.

In this embodiment, the substance portions of the first substance and the substance portions of the second substance are present in separate tracks.

Alternatively, the substance portions of the first substance N1 and the substance portions of the second substance N2 can be present in one or more common tracks; cf. FIG. 19.

A third substance N3, e.g. an inert substance, can be arranged between the track of the first substance N1 and the track of the second substance N2; cf. FIG. 24.

FIG. 24 shows a further embodiment of a multi-component system according to the invention.

The figure description of FIG. 24 is essentially the same as the figure description of FIG. 23.

Between the tracks of the first substance N1 and the path of the second substance N2, a third substance N3 is applied, in this case an inert substance.

FIG. 25 shows a further embodiment of a multi-component system according to the invention.

A multi-component system of a first substance N1, a second substance N2, a third substance N3 and a fourth substance N4 is shown, wherein the first substance N1, the second substance N2, the third substance N3 and the fourth substance N4 are present in multiple substance portions.

In this embodiment, one portion of the first substance N1, one portion of the second substance N2, one portion of the third substance N3, and one portion of the fourth substance N4 are each arranged in a respective capsule K, in particular a nanocapsule and/or microcapsule.

In this embodiment, the substance portions of the first substance N1, the second substance N2, the third substance N3 and the fourth substance N4 are provided on a surface OF.

In this embodiment, the substance portions of the first substance N1 and the substance portions of the second substance N2 are arranged at a defined distance from each other.

The substance portions of the first substance N1 and the substance portions of the second substance N2 are arranged in the form of a track on the surface OF.

The substance portions of the third substance N3 and the substance portions of the fourth substance N4 are arranged in the form of a track on the surface OF.

In this embodiment, the substance portions of the third substance N3 and the substance portions of the fourth substance N4 are arranged at a defined distance from each other.

In particular, both the distance between the individual substance portions of a substance (N1. N2, N3 or N4) and the distance between the substance portions of the different substances are defined.

Alternatively, only the distance between the individual substance portions of one substance (N1, N2, N3 or N4) or the distance between the substance portions of the different substances can be defined.

Alternatively and/or additionally, the substance portions of the first substance N1 and/or the substance portions of the second substance N2 and/or the substance portions of the third substance and/or the substance portions of the fourth substance N4 can be arranged at a non-defined distance from each other.

In one embodiment of FIG. 25, the first substance N1 can be a first component of a two-component adhesive.

Alternatively, the first substance can be a silicone adhesive or a one-component adhesive.

In one embodiment of FIG. 25, the second substance N2 can be a second component of a two-component adhesive.

Alternatively, the second substance N2 can be a silicone adhesive, plastic adhesive, or polyurethane adhesive.

In one embodiment of FIG. 25, the third substance N3 can be a first component of a two-component adhesive.

Alternatively, the third substance N3 can be a silicone adhesive or a one-component adhesive.

In one embodiment of FIG. 25, the fourth substance N4 can be a second component of a two-component adhesive.

Alternatively, the fourth substance N4 can be a silicone adhesive, plastic adhesive, or polyurethane adhesive.

FIG. 26 shows a further embodiment of a multi-component system according to the invention.

A multi-component system of a first substance N1, a second substance N2 and a third substance N3 is shown, wherein the first substance N1, the second substance N2 and the third substance N3 are present in multiple substance portions.

In this embodiment, one portion of the first substance N1, one portion of the second substance N2 and one portion of the third substance N3 are each arranged in a respective capsule K, in particular a nanocapsule and/or microcapsule.

In this embodiment, the substance portions of the first substance N1, the second substance N2 and the third substance N3 are provided on a surface OF.

In this embodiment, the substance portions of the first substance N1 and the substance portions of the second substance N2 are arranged at a defined distance from each other.

The substance portions of the first substance N1 and the substance portions of the second substance N2 are arranged in the form of a track on the surface OF.

The substance portions of the third substance N3 are arranged in the form of a track on the surface OF.

In this embodiment, the substance portions of the third substance N3 are arranged at a defined distance from each other.

In particular, both the distance between the individual substance portions of each substance (N1, N2, N3) and the distance between the substance portions of the different substances (N1, N2) are defined.

Alternatively, only the distance between the individual substance portions of each substance (N1, N2, N3) or the distance between the substance portions of the different substances can be defined.

Alternatively and/or additionally, the substance portions of the first substance N1 and/or the substance portions of the second substance N2 and/or the substance portions of the third substance can be arranged at a non-defined distance from each other.

In one embodiment of FIG. 28, the first substance N1 can be a first component of a two-component adhesive.

Alternatively, the first substance can be a silicone adhesive or a one-component adhesive.

In one embodiment of FIG. 28, the second substance N2 can be a second component of a two-component adhesive.

Alternatively, the second substance N2 can be a silicone adhesive, plastic adhesive, or polyurethane adhesive.

In one embodiment of FIG. 26, the third substance N3 can be a silicone adhesive or polyurethane adhesive.

In embodiments of FIGS. 15-26, the volume of the one or more substance portions of the at least one first substance N1 can be substantially in a defined ratio to the volume of the one or more substance portions of the at least one second substance N2, so that a defined mixing ratio of the substances is achieved when mixing the one or more substance portions of the at least one first substance N1 with the one or more substance portions of the at least one second substance N2.

In particular, the volumes and the mixing ratio can be selected in such a way that the product of the mixing of the substances results in an effect that goes beyond the effect of the individual substances.

In embodiments of FIGS. 15-28, the arrangement of the one or more substance portions of the at least one first substance N1 and the arrangement of the one or more substance portions of the at least one second substance N2 on the surface OF, in particular during activation, e.g. by pressure, ultrasound, temperature change, etc., can be used to achieve a mixing of the substances, in particular an optimal mixing of the substances, and thus a desired property of the resulting hybrid substance, e.g. during bonding of the surface OF with a further surface OF, a mixing of the substances, in particular an optimum mixing of the substances, and thus a desired property of the resulting hybrid substance can be achieved.

FIG. 27, FIG. 28, FIG. 29, FIG. 30, FIG. 31, and FIG. 32 show embodiments of multi-component systems according to the invention, each embedded in an environmental matrix.

In each case, a multi-component system with a first substance N1 and a second substance N2 is shown, wherein the first substance N1 and the second substance N2 are present in multiple substance portions.

Each portion of the first substance N1 and of the second substance N2 is arranged in a respective capsule K, in particular a nanocapsule and/or microcapsule.

The substance portions of the first substance N1 and the substance portions of the second substance N2 are provided on a surface OF.

The surface OF a metal surface.

Alternatively, the surface OF can be a wood surface, plastic surface, paper surface, textile surface, film, or the like.

The capsules are embedded in an environmental matrix (FIG. 27: environmental matrix is an acrylic paint; FIG. 28: environmental matrix is an acrylic varnish; FIG. 29: environmental matrix is a water-based adhesive 1; FIG. 30: environmental matrix is a water-based adhesive 2; FIG. 31: crosslinking adhesive 1; FIG. 32: crosslinking adhesive 2).

Possible application patterns of the environment matrix are conceivable, for example, analogous to the application patterns in FIGS. 15-20 and 22-25.

FIG. 33 shows the increased effect of a hybrid adhesive compared with the use of the individual components.

In this embodiment, the adhesive strength of a hybrid adhesive system according to the invention comprising two different adhesives was compared with the adhesive strength of the individual adhesives.

For this purpose, as a first control, aluminum was bonded to aluminum using an epoxy adhesive (first bar from the left).

Furthermore, as a second control, plastic was bonded to plastic using an epoxy adhesive (second bar from the left).

Furthermore, as a third control, aluminum was bonded to aluminum using a polyurethane adhesive (middle bar).

Furthermore, as a fourth control, plastic was bonded to plastic using a polyurethane adhesive (second bar from the right).

The use of the combination of epoxy adhesive and polyurethane adhesive (right bar) shows higher bond strength when bonding aluminum and plastic compared to the bond strength of the controls.

FIGS. 34A-34D shows a comparison of pre-applied multi-component systems of the invention, in which the systems were applied to aluminum test specimens with environmental medium via the ASTM D823 standard procedure with a layer thickness of 200 μm.

Here, FIG. 34A shows a two-component system of the invention without bonding in the inactivated state. In FIG. 34B, the system shown in FIG. 34A has been activated at 160° C. Thereby, FIG. 34C shows a two-component system of the invention with linkage between the capsules in the inactivated state. In FIG. 34D, the system shown in FIG. 34C has been activated at 160° C. It can be seen that the adhesive application is significantly more homogeneous with the capsules linked to one another than without linkage. This can be seen both before activation of the adhesive and after activation at 160° C.

Specimen cleaning prior to bonding was performed according to EN 13887. Adhesive application was performed according to ASTM D823 with an adhesive layer length of 12.5 mm×25 mm according to DIN1465.

Thereby, the capsules used were produced according to the following procedure.

In a first solution (solution 1), the resin component is dissolved in 10 mL of dichloromethane (DCM). In a second solution (solution 2), 9 g of SDS is dissolved in $H_2O$. After both the resin and SDS are dissolved in solutions 1 and 2, solution 1 is heated to 26° C. Solution 1 is then added dropwise to solution 2, thereby encapsulating the resin component. The solution is then stirred at 30° C. for 30 min. Then, after 30 min, a 6% SDS solution is added and the temperature is raised to 35° C. so that the remaining solvent evaporates. To remove the encapsulated resin component from the remaining solvent, the solution is centrifuged at 3000 rpm for 3 min and the supernatant is removed. Alternatively, the microcapsules can be extracted via complete evaporation of the solvent.

An equivalent procedure can be followed with the hardener and the silicone component.

Crosslinking of the Microcapsule Shells

The degree of crosslinking of the microcapsules can be used to determine the discharge (or activation) of the contents of the capsules. The lower the degree of crosslinking, the faster and more content is discharged.

Adjustment of the Degree of Crosslinking Via a Co-Component:

By adding a second component to the shell material such as PMMA, an additional crosslinker such as SDS can be added. Different amounts of SDS were used (2 wt.-%; 4 wt.-%, 6 wt.-%, and 9 wt.-%). The more SDS is used in combination with PMMA in DCM, the higher the degree of crosslinking of the shell that is formed.

Setting the Degree of Crosslinking Via UV Crosslinking

A radical polymerization is photo-induced. The procedure is the same as in the previous example. However, instead of using PMMA as the shell material, MMA is used. Exposure to 254 nm UV light converts the MMA to PMMA, thus generating crosslinking and subsequently the shell material. The degree of crosslinking depends on the average length of the MMA polymer, as well as the duration of exposure to UV light. The longer the polymer, or the shorter the exposure to UV light, the lower the degree of crosslinking of the shell material.

Setting the Degree of Crosslinking Via the Number of Functional Groups of the Shell Material As in the examples described above, the shell material has functional groups that crosslink with each other during the formation of the shell, thus forming the shell of the microcapsule. The more functional groups the polymer has, the higher the degree of crosslinking. In linear polymers, functional groups can be linked to a backbone, or In star polymers, to the many backbones of the polymer chain.

Setting the Size of the Microcapsule

In the above example, the different size of the microcapsules is achieved by a change in pH. The hardener component consists of amine derivatives and, with a pH of 9, has a significantly lower pH than the resin component, which consists of bisphenol derivatives with a pH of 6.

Alternatively, the microcapsule size can be adjusted by the stirring speed, viscosity of the materials to be encapsulated, via the size of the opening of the capillary in microfluidic systems, spray drying and/or dripping methods, number of shells or the like.

Determination of the Size Distribution

The size distribution of the capsules was performed using the Keyence VHX 7000 digital microscope. The size of the microcapsules was determined by measuring the diameter of the microcapsules. The size distribution was measured using a microscope internal program.

The microcapsules can be linked according to the process described, for example, in international applications WO2020/193526 and WO2020/193536.

The microcapsules are prepared as described above via free-radical polymerization of MMA in a first batch process. By this process, the microcapsule has carboxyl groups on the entire surface. Similarly, the second microcapsule component is prepared in a second batch. Subsequently, the carboxyl groups of the surface of the two components are activated in separate batches with a mixture of 3:1 NHS/EDC for 1 h at room temperature. Subsequently, the microcapsules are centrifuged and washed. In the next step, a diamine is added in excess to the microcapsules with the hardener component. Via coupling with the activated carboxyl groups, one of the terminal amine groups binds with the carboxyl group. Since the amine has been added in excess, the second terminal amine is freely available on the surface of the hardener component for binding of the second microcapsule. Afterwashing and centrifugation, the resin component with the activated carboxyl groups is combined with the hardener component with the terminal amine groups on the surface. Via the reaction of the activated carboxyl groups with the terminal amine groups. Due to the different size of the two components, as well as the steric effects and the limited number of functional groups on the surface of the microcapsules, an ideal mixing ratio of the two components can be achieved.

FIG. 35 shows the result of tests of the multi-component systems according to the invention with a silicone (Elastosil® E43).

In this application example, the adhesive effect of a multi-component system according to the invention was tested, in which a two-component epoxy adhesive was encapsulated together with a one-component silicone. Here, the capsules containing the components of the epoxy adhesive are linked to one another. A 50:50 mixture (epoxy adhesive to silicone) was applied to an aluminum surface.

Subsequently, an adhesive paste containing the two microencapsulated adhesives was applied to the metal surface and dried at 40° C. for 30 min.

The adhesive layer applied in this way has no tacticity and is therefore neither tacky nor reactive. Thus, the adhesive layer can be activated only when needed and can be processed independently of the dripping time.

By combining the epoxy adhesive with silicone adhesive, an increase in the bond strength of the silicone adhesive could be achieved.

For this purpose, the specimens were bonded according to DIN 1465 and the adhesion force was determined by means of a notch in a tensile test. The following parameters must be taken into account when bonding according to DIN 1465:

The tests according to DIN 465 allow conclusions to be drawn in particular on bonding strength, quality of the adhesives, aging behavior and adhesive processing.

Specimen geometry:

b: Specimen width (25 mm)

l: specimen length (100 mm)

L_2: Adhesive layer length (12.5 mm)

Joining part:

100×25×1.6 mm

Bonding:

12.5×25 mm

Number of repetitions per test: 6

Test speed: specimen must be destroyed within 65+/−20 s when loaded.

Influences on tensile shear tests:

Adhesive, room temperature, test speed, age of specimens, adhesive thickness.

By combining the adhesives in the system according to the invention, a 7-times higher adhesive strength could be achieved than with the silicone adhesive.

Figure 36:
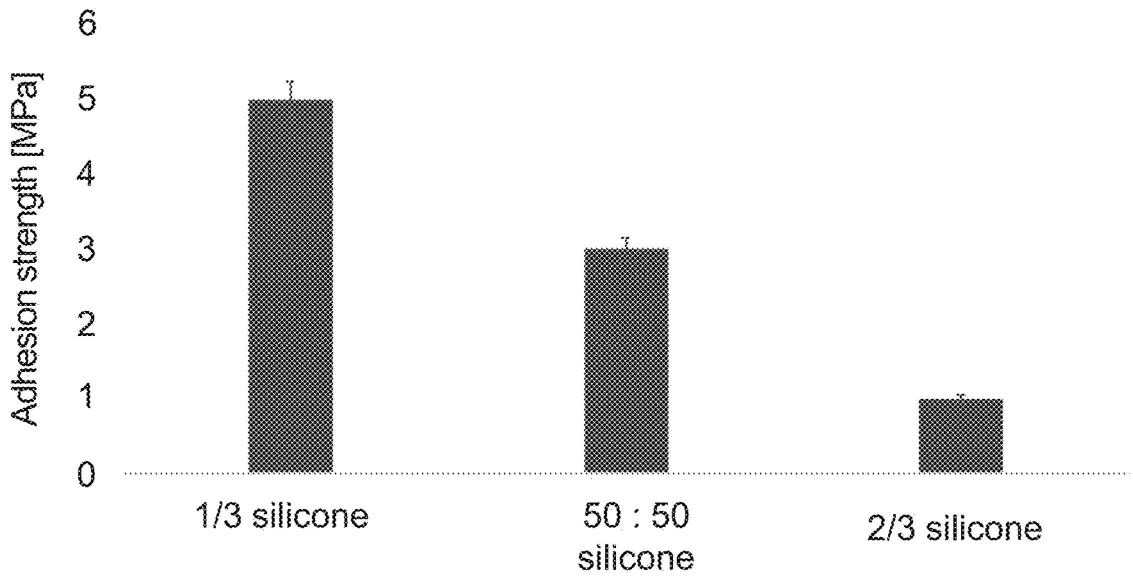
FIG. 36 shows a comparison of the adhesive strength of a multi-component system according to the invention with different mixing ratios of silicone and epoxy adhesive.

FIG. 36 shows the result of further investigations of the multi-component system of the invention described in FIG. 25.

The adhesion strength was investigated when different ratios of epoxy adhesive and silicone were used.

The test setup is equivalent to that described for FIG. 35.

The following ratios of epoxy adhesive:silicone were tested in the multi-component systems according to the invention: 3:1, 1:1, and 1:3.

A correlation is shown between the increase in adhesive strength and the quantity of epoxy adhesive used. These tests show that the desired adhesion strength can be precisely adjusted by the ratio of epoxy adhesive to silicone via the respective amounts of the capsules or the various substances used in the multi-component system according to the invention. Thus, the system according to the invention allows the desired properties of both components to be adjusted.

In connection with the present invention, the following aspects are now further explicitly disclosed:

Aspect 1: Multi-component system with at least one first substance (N1) and at least one second substance (N2), wherein the multi-component system can be activated, wherein the first substance (N1) and the second substance (N2) are present in one or more substance portions.

Aspect 2: Multi-component system according to aspect 1, characterized in that the multi-component system can be activated.

Aspect 3: Multi-component system according to aspect 1 or aspect 2, characterized in that the first substance portions are formed with at least one first functional group (R2) and provided with a first linker (L1), and wherein the second substance portions are formed with at least one second functional group (R21) and provided with a second linker (L2), wherein the first functional group (R2) reacts via a predefined interaction with the second functional group (R21) and links them to one another, and wherein the distance of the functional groups to the respective substance portion is determined by the respective linker (L).

Aspect 4: Multi-component system according to aspect 3, characterized in that the first linker (L1) is longer than the second linker (L2) or vice versa.

Aspect 5: Multi-component system according to any one of the preceding aspects, characterized in that the first substance portions and the second substance portions differ in that the first substance portions are linked or linkable to a greater number of substance portions than the second substance portions or vice versa.

Aspect 6: Multi-component system according to any one of the preceding aspects, characterized in that the functional groups (R) are formed homogeneously or heterogeneously.

Aspect 7: Multi-component system according to any one of the preceding aspects, characterized in that the first substance portions have a substantially identical size and/or in that the second substance portions have a substantially identical size.

Aspect 8: Multi-component system according to any one of the preceding aspects, characterized in that the first substance portions and the second substance portions have a different size.

Aspect 9: Multi-component system according to any one of the preceding aspects, characterized in that the multi-component system has a network structure with interspaces, wherein the network structure is formed by substance portions of the first substance, wherein at least one substance portion of the second substance is, at least in sections, arranged in each of the interspaces.

Aspect 10: Multi-component system according to any of the preceding aspects, characterized in that a substance portion of the first substance (N1) and/or the second substance (N2) is arranged in a capsule (K), in particular a nanocapsule and/or microcapsule.

Aspect 11: Multi-component system according to any one of the preceding aspects, characterized in that a capsule (K1) for the first substance (N1) has a different size than a capsule (K2) for the second substance (N2), in particular wherein the capsule (K1) for the first substance (N1) is larger than the capsule (K2) for the second substance (N2).

Aspect 12: Multi-component system according to aspect 10 or aspect 11, characterized in that the capsules (K1) for the first substance (N1) have an identical size.

Aspect 13: Multi-component system according to any one of the preceding aspects, characterized in that activation of the multi-component system is achieved by at least one of a change in pressure, pH, UV radiation, osmosis, temperature, light intensity, humidity, or the like.

Aspect 14: Multi-component system according to any one of the preceding aspects, characterized in that the first substance (N1) and the second substance (N2) are components of a multi-component adhesive, in particular a two-component adhesive.

Aspect 15: Method of preparing a multi-component system with at least one first substance and at least one second substance, the first substance and the second substance being present in multiple substance portions, wherein the multi-component system can be activated, comprising the steps of:

the first substance portions are formed with at least one first functional group (R2) and provided with a first linker (L1), the second substance portions are formed with at least one second functional group (R21) and provided with a second linker (L2), the first functional group (R2) reacts via a predefined interaction with the second functional group (R21) so that they are linked to one another, and the distance of the functional groups (R2, R21) to the respective substance portion is determined by the respective linker (L).

Aspect 16: Method according to aspect 16, characterized in that the first substance portions are formed with at least one third functional group (R1) and provided with a third linker (L3), wherein the third functional group (R1) each comprises at least one protection group (SG), so that only correspondingly functionalized substance portions of the first substance can bind to the substance portions of the first substance, and wherein the method further comprises at least the step that the protection groups (SG) are initially present and are only removed when the substance portions are to be linked to one another via the third functional groups (R1).

Aspect 17: Method of aspect 15 or aspect 16, characterized in that the multi-component system is a multi-component system according to any one of aspects 1 to 14.

REFERENCE SIGN

B Adhesive tape
C Core, Core
K Capsule/Capsule Population
K1 Capsule 1/capsule population 1
K2 Capsule 2/capsule population 2
K3 Capsule 3/capsule population 2
Kn Capsule n/capsule population n
KG Gas capsule
L Linker
L1 Linker 1
L2 Linker 2
N1 Substance 1
N2 Substance 2
OF Surface
R Functional group
R1 Functional group 1
R2 Functional group 2
R21 Functional group 21
S Capsule, shell
S1 Step 1
S2 Step 2
S3 Step 3
S4 Step 4
SG Protection group
UM environment matrix

The invention claimed is:

1. A multi-component system, comprising:

a first substance N1, and a second substance N2, wherein the first substance N1 is contained in a first capsule K1 and the second substance N2 is contained in a second capsule K2, and wherein the first capsule K1 and the second capsule K2 are covalently linked to one another by a linker L1 arranged on the first capsule K1 and a linker L2 arranged on the second capsule K2, and wherein the first substance N1 in the first capsule K1 comprises a pharmaceutically active ingredient.

2. The multi-component system according to claim 1, wherein a linkage between the first capsule K1 and the second capsule K2 is achieved via a bridge, wherein the bridge is formed by a linkage of a linker L1 arranged on the first capsule K1 and a linker L2 arranged on the second capsule K2.

3. The multi-component system according to claim 2, wherein the linker L1 and the linker L2 are each selected from the group consisting of star polymers, biopolymers, alkanes, alkenes, alkynes, aliphatic chains, proteins, silk, polysaccharides, cellulose, starch, chitin, nucleic acid, synthetic polymers, homopolymers, polyethylenes, polypropylenes, polyvinyl chloride, polylactam, natural rubber, polyisoprene, copolymers, random copolymers, gradient copolymer, alternating copolymer, block copolymer, graft copolymers, acrylonitrile butadiene styrene (ABS), styrene acrylonitrile (SAN), butyl rubber, polymer blends, polymer alloys, inorganic polymers, polysiloxanes, polyphosphazenes, polysilazanes, ceramics, basalt, isotactic polymers, syndiotactic polymers, atactic polymers, crosslinked polymers, elastomers, thermoplastic elastomers, thermosetting polymers, semi-crystalline linkers, thermoplastics, cis-trans polymers, conducting polymers, linear polymers, polymers with multivalence, star-shaped polyethylene glycols, self-assembled monolayers (SAM), carbon nanotubes, ring-shaped polymers, dendrimers, ladder polymers and similar substances, supramolecular polymers, and any other type of linkage of the first capsule K1 and the second capsule K2 with a functional group.

4. The multi-component system according to claim 3, wherein the functional group is selected from the group consisting of alkanes, cycloalkanes, alkenes, alkynes, phenyl substituents, benzyl substituents, vinyl, allyl, carbenes, alkyl halides, phenol, epoxides, ethers, peroxides, ozonides, aldehydes, hydrates, imines, oximes, semicarbazones, hemiacetals, hemiketals, lactols, acetal/ketal, aminals, carboxylic acid, carboxylic acid esters, lactones, orthoesters, anhydrides, imides, carboxylic acid halides, carboxylic acid derivatives, amides, lactams, peroxyacids, nitriles, carbamates, guanidines, carbodiimides, amines, aniline, hydroxylamines, hydrazines, hydrazones, azo compounds, nitro compounds, thiols, mercaptans, sulfides, phosphines, P-Ylene, P-Ylides, biotin, streptavidin, metallocenes, and the like.

5. The multi-component system according to claim 1, wherein the first substance N1 in the first capsule K1 comprises an adhesive or a component of a multi-component adhesive.

6. The multi-component system according to claim 1, wherein the second substance N2 in the second capsule K2 comprises at least one component of a multi-component adhesive, wherein the multi-component adhesive is selected from the group consisting of epoxy adhesives and polyurethane adhesives.

7. The multi-component system according to claim 1, further comprising:

at least one further substance N3, which is arranged in a capsule K3.

8. The multi-component system according to claim 7, wherein the at least one further substance N3 in the capsule K3 comprises an adhesive, a component of a multi-component adhesive, or a sealing material.

9. The multi-component system according to claim 7, wherein a shell of the first capsule K1, the second capsule K2, and/or the capsule K3 comprises at least one material selected from the group consisting of (co)polymer, wax, resin, protein, polysaccharide, gum arabic, maltodextrin, inulin, metal, ceramic, acrylate (co)polymer, microgel, phase change material, lipids, maleic formaldehydes, carbohydrates, and combinations thereof.

10. A material, to which the multi-component system according to claim 1 is applied.

11. A method, comprising:

treating a wound with the multi-component system according to claim 1.

12. The multi-component system according to claim 1, wherein the first capsule K1 and the second capsule K2 are nanocapsules and/or microcapsules.

13. The multi-component system according to claim 1, wherein the second substance N2 in the second capsule K2 comprises an adhesive or a component of a multi-component adhesive system.

* * * * *